United States Patent
Rawicz et al.

(10) Patent No.: US 9,924,895 B2
(45) Date of Patent: Mar. 27, 2018

(54) METHOD AND APPARATUS FOR A SPECTRAL DETECTOR FOR NONINVASIVE DETECTION AND MONITORING OF A VARIETY OF BIOMARKERS AND OTHER BLOOD CONSTITUENTS IN THE CONJUNCTIVA

(71) Applicant: LivSpek Medical Technologies Inc., West Vancouver (CA)

(72) Inventors: Andrew H. Rawicz, Burnaby (CA); Sara Moghaddamjoo, West Vancouver (CA); Bruno Jaggi, Vancouver (CA)

(73) Assignee: LivSpek Medical Technologies Inc., West Vancouver, BC (CA)

( * ) Notice: Subject to any disclaimer, the term of this patent is extended or adjusted under 35 U.S.C. 154(b) by 0 days.

(21) Appl. No.: 15/710,031

(22) Filed: Sep. 20, 2017

(65) Prior Publication Data

US 2018/0042527 A1 Feb. 15, 2018

Related U.S. Application Data

(63) Continuation of application No. PCT/IB2016/051893, filed on Apr. 1, 2016.
(Continued)

(51) Int. Cl.
*A61B 5/1455* (2006.01)
*A61B 5/00* (2006.01)
(Continued)

(52) U.S. Cl.
CPC .......... *A61B 5/1455* (2013.01); *A61B 3/0008* (2013.01); *A61B 3/14* (2013.01);
(Continued)

(58) Field of Classification Search
CPC . A61B 5/1455; A61B 5/14551; A61B 5/6803; A61B 5/6821
See application file for complete search history.

(56) References Cited

U.S. PATENT DOCUMENTS

| | | | |
|---|---|---|---|
| 5,873,831 A | 2/1999 | Bernstein et al. | |
| 6,044,285 A | 3/2000 | Chaiken et al. | |

(Continued)

FOREIGN PATENT DOCUMENTS

| | | |
|---|---|---|
| CN | 203873762 U | 10/2014 |
| EP | 0242258 A1 | 10/1987 |

(Continued)

OTHER PUBLICATIONS

International Search Report and Written Opinion dated May 11, 2016 for International Application No. PCT/IB2016/051893.
(Continued)

*Primary Examiner* — Eric Winakur
(74) *Attorney, Agent, or Firm* — Wilson Sonsini Goodrich & Rosati

(57) ABSTRACT

A specialized spectrometer comprises a light source to generate a monochromatic light beam to generate resonance Raman peaks or resonance near infrared absorption peaks from a region of the subject and a reference light source to illuminate the region with a reference light beam. The light energy from the resonance Raman peaks can be measured with a detector coupled to an optical wavelength separator. A portion of the reference beam scattered from the region can be measured with a reference detector. An amount of the constituent can be determined with a processor in response to the resonance Raman peaks measured with the detector and the portion of the reference beam measured with the reference detector. The illumination of the region with reference beam with the monochromatic beam allows accurate determination of the amount of the constituent, and the
(Continued)

amount may comprise a concentration, such as an amount per unit volume.

20 Claims, 9 Drawing Sheets

Related U.S. Application Data

(60) Provisional application No. 62/142,228, filed on Apr. 2, 2015, provisional application No. 62/147,265, filed on Apr. 14, 2015.

(51) Int. Cl.
*A61B 3/14* (2006.01)
*A61B 3/00* (2006.01)

(52) U.S. Cl.
CPC .......... *A61B 5/6803* (2013.01); *A61B 5/0075* (2013.01); *A61B 5/6821* (2013.01); *A61B 2560/0223* (2013.01); *A61B 2562/146* (2013.01)

(56) References Cited

U.S. PATENT DOCUMENTS

| | | | |
|---|---|---|---|
| 6,574,501 B2 | 6/2003 | Lambert et al. | |
| 6,721,583 B1 | 4/2004 | Durkin et al. | |
| 6,868,285 B2 | 3/2005 | Muller et al. | |
| 6,961,599 B2 * | 11/2005 | Lambert | A61B 5/1455 600/318 |
| 7,039,452 B2 | 5/2006 | McClane et al. | |
| 7,107,092 B2 | 9/2006 | Goldstein et al. | |
| 7,209,773 B2 | 4/2007 | Iuliano | |
| 7,233,817 B2 | 6/2007 | Yen | |
| 7,304,722 B2 | 12/2007 | Iuliano | |
| 7,627,357 B2 * | 12/2009 | Zribi | A61B 5/14532 600/310 |
| 8,380,270 B2 | 2/2013 | Menon | |
| 8,385,997 B2 | 2/2013 | Hyde et al. | |
| 8,452,362 B2 | 5/2013 | Menon | |
| 8,515,506 B2 | 8/2013 | Ridder et al. | |
| 8,553,219 B2 | 10/2013 | Patil et al. | |
| 8,740,384 B2 | 6/2014 | Hirono | |
| 8,864,219 B2 | 10/2014 | Jansen | |
| 8,989,848 B2 | 3/2015 | Rorabaugh et al. | |
| 2002/0016534 A1 * | 2/2002 | Trepagnier | A61B 5/1455 600/316 |
| 2002/0095257 A1 | 7/2002 | Rosen et al. | |
| 2004/0063216 A1 | 4/2004 | Lubocki | |
| 2004/0180379 A1 | 9/2004 | Van et al. | |
| 2005/0113678 A1 | 5/2005 | Villard et al. | |
| 2006/0258920 A1 | 11/2006 | Burd et al. | |
| 2008/0009688 A1 | 1/2008 | Dahlen et al. | |
| 2008/0117416 A1 | 5/2008 | Hunter et al. | |
| 2008/0318247 A1 | 12/2008 | Chang et al. | |
| 2009/0118601 A1 | 5/2009 | Rabolt et al. | |
| 2009/0234202 A1 | 9/2009 | Goix et al. | |
| 2010/0105098 A1 | 4/2010 | Frederiske et al. | |
| 2013/0018237 A1 | 1/2013 | Henneberg et al. | |
| 2014/0357969 A1 | 12/2014 | Wada et al. | |

FOREIGN PATENT DOCUMENTS

| | | |
|---|---|---|
| WO | WO-2006130921 A1 | 12/2006 |
| WO | WO-2015183994 A1 | 12/2015 |
| WO | WO-2016015052 A1 | 1/2016 |

OTHER PUBLICATIONS

Moghaddamjoo, et al., Characterization of Cardiac troponin I raman signature in bovine serum albumin and human blood serum for the potential diagnosis of myocardial infarction. Nat Prod Chem Res. 2015; 4(1): 5 pages.
Moghaddamjoo,S. Prevention of myocardial infarctions, using non invasive biophotonics measurement of biomarker cardiac troponin I. Master's thesis, Simon Fraser University, Fall 2010.
Shih, et al., Non-invasive glucose sensing with raman spectroscopy. Massachusetts Institute of Technology, 2007. 43 Pages.
So, et al., Recent advances in noninvasive glucose monitoring. Medical devices: Evidence and research, Dovepress Journal. Jun. 27, 2012; 5: 45-52.
Tashakor, A. P., Detection of cardiac troponin I in circulation using Raman spectroscopy; an approach to prediction of myocardial infarction, Master's thesis, Simon Fraser University. Apr. 2012. 131 Pages.
Owen, et al., Diabetes and the tortuosity of vessels of the bulbar conjunctiva. Ophthalmology. Jun. 2008;115(6):e27-32. doi: 10.1016/j.ophtha.2008.02.009.
Resonant vs non-resonant raman spectroscopy. UC Davis Chem wiki. Mar. 6, 2015, Available at:https://chem.libretexts.orgi@api/deki/pages/1851/pdf/Resonant%2bvs.%2bNonresonant%2bRaman%2bSpectroscopy.pdf?stylesheet=default.

* cited by examiner

Legend:

☐ NIR LEDs

○ Photodiodes

■ Green LED for eye positioning

METHOD AND APPARATUS FOR A SPECTRAL DETECTOR FOR NONINVASIVE DETECTION AND MONITORING OF A VARIETY OF BIOMARKERS AND OTHER BLOOD CONSTITUENTS IN THE CONJUNCTIVA

CROSS-REFERENCE

This application is a continuation of PCT/IB2016/051893, filed on 1 Apr. 2016, entitled "METHOD AND APPARATUS FOR A SPECTRAL DETECTOR FOR NONINVASIVE DETECTION AND MONITORING OF A VARIETY OF BIOMARKERS AND OTHER BLOOD CONSTITUENTS IN IN THE CONJUNCTIVA"; which is a non-provisional of and claims the benefit of U.S. Provisional Application No. 62/142,228, filed on 2 Apr. 2015, entitled "METHOD AND APPARATUS FOR A SPECTRAL DETECTOR FOR NONINVASIVE DETECTION AND MONITORING OF A VARIETY OF BIOMARKERS AND OTHER BLOOD CONSTITUENTS IN THE CONJUNCTIVA"; and U.S. Provisional Application No. 62/147,265, filed on 14 Apr. 2015, entitled "METHOD AND APPARATUS FOR A SPECTRAL DETECTOR FOR NONINVASIVE DETECTION AND MONITORING OF A VARIETY OF BIOMARKERS AND OTHER BLOOD CONSTITUENTS IN THE CONJUNCTIVA", the entire disclosures of which are incorporated herein by reference.

BACKGROUND

Prior methods and apparatus of non-invasively measuring subjects optically are less than ideal in at least some respects. For example, prior methods and apparatus of measuring blood of a subject can be less accurate than would be ideal. Also, alignment of the subject with the measurement apparatus can be challenging. Many of the prior art spectrometers are less than ideally suited to measure constituents non-invasively in vivo. Although prior methods and apparatus may measure blood spectroscopically in a controlled laboratory environment, these methods generally involve the removal of blood from the subject, which can be inconvenient and somewhat painful in at least some instances.

SUMMARY

The specialized spectrometer methods and apparatus disclosed herein are particularly well suited for accurate non-invasive measurements of subjects. Although reference is made to measuring constituents of blood, the methods and apparatus disclosed herein can be used to non-invasively measure constituents in many tissues and bodily fluids including tears, saliva, or sweat.

In many embodiments, the specialized spectrometer comprises a light source to generate a monochromatic light beam to generate resonance Raman peaks from a region of the subject and a reference light source to illuminate the region with the reference light beam. The light energy from the resonance Raman peaks can be measured with a detector coupled to an optical wavelength separator. A portion of the reference beam scattered from the region can be measured with a reference detector. An amount of the constituent can be determined with a processor in response to the resonance Raman peaks measured with the detector and the portion of the reference beam measured with the reference detector. The illumination of the region with reference beam with the monochromatic beam allows accurate determination of the amount of the constituent, and the amount may comprise a concentration, such as an amount per unit volume. The constituent measured with resonance Raman spectroscopy may comprise a constituent of blood, such as a molecule, and the portion of scattered light measured with the reference detector may correspond to a second constituent of blood that that provides a measurable signal with the reference beam, for example hemoglobin. The spectrometer can be configured in many ways, such as with a table top configuration or wearable configuration carried by the subject.

The methods and apparatus disclosed herein can also provide improved safety. The processor can be configured with instructions to detect the presence of blood vessels with the reference beam in order to ensure that an appropriate region of the subject is aligned with the delivery system, and the processor configured with instructions to direct the monochromatic beam to the region in response to the portion of the reference beam measured with the detector. This approach can allow for increased amounts of light energy of the monochromatic beam when used near delicate structures such as an eye.

In one aspect, disclosed herein is a spectrometer to non-invasively measure a blood constituent through an epithelium and vessel walls of blood vessels at a region of a subject with light. The spectrometer comprises a light source to generate a monochromatic light beam, the monochromatic beam comprising one or more wavelengths having a frequency at an electronic excitation of the blood constituent to generate resonance Raman peaks. The spectrometer further comprises an optical system to deliver the monochromatic light beam through the epithelium and vessel walls to the blood constituent at the region, and receive light energy from the blood constituent through the epithelium and the vessel walls. The optical system may comprise an optical wavelength separator to selectively transmit the resonance Raman peaks. The spectrometer further comprises a detector coupled to the optical delivery system to measure the resonance Raman peaks from the blood constituent at the region. The optical system further comprises a reference light source to generate a reference beam to illuminate blood at the region. The optical system further comprises a reference detector to measure a portion of the reference beam backscattered from the blood at the region. The spectrometer further comprises a processor coupled to the detector. The processor may be configured with instructions to measure the resonance Raman peaks from the detector and the portion from the reference detector in order to determine an amount of the blood constituent from the resonance Raman peaks and the portion of the reference beam backscattered from the blood at the region.

The processor may be coupled to the light source and configured to transmit the monochromatic light beam to the region with an amount of energy greater than the reference beam. The processor may be configured to detect a presence of the blood vessels with the portion of the reference beam and transmit the monochromatic beam in response to the presence of the blood vessel.

The amount of energy of the monochromatic beam may exceed an eye safe threshold of the measurement beam, and the reference beam may not exceed an eye safe threshold of the reference beam. The processor may be configured to transmit the reference beam and not to transmit the monochromatic light beam when the presence of the blood vessels has not been detected.

The region may comprise a volume of blood and the reference beam and reference detector may be configured to measure a second constituent of blood, wherein the second constituent may comprise a greater amount by volume than the constituent of interest.

The optical system may be configured to focus the monochromatic light beam on a blood vessel beneath the epithelium. The optical system may be further configured to receive the resonance Raman peaks from the blood constituent through the epithelium and direct the resonance Raman peaks to the detector. The optical system may comprise a focusing element to collect the backscattered light from a region of the tissue. The focusing element may comprise one or more of a lens, an objective lens, a reflector, a curved reflector, a spherical reflector, or a curved reflector with an aperture, a concave reflector with an aperture, a convex reflector, a convex reflector aligned with an aperture of a concave reflector or Schwarzschild optics. The focusing element may be configured to receive light from the region and transmit the resonance Raman peaks in a substantially collimated configuration toward the detector.

The monochromatic light source may be transmitted toward the region in a substantially collimated configuration. The optical system may comprise an optical path along which the resonance Raman peaks and the portion are transmitted coaxially toward the detector and the reference detector.

The processor may be coupled to the reference detector and configured to determine the amount of the constituent in response to an intensity of the portion of the beam received from the tissue and an intensity of the resonance Raman peaks. The processor may be coupled to the reference detector and configured to determine a concentration of the constituent in blood in response to an intensity of the portion of the beam received from the tissue and an intensity of the resonance Raman peaks. The processor may be coupled to the reference detector and configured to determine a concentration of the constituent in response to an intensity of the portion of the beam received from the tissue and an intensity of the resonance Raman peaks, the concentration comprising the amount of the constituent per unit volume of the blood.

The wavelength separator may be configured to separate non-resonance Raman light energy from the resonance Raman peaks, wherein the non-resonance Raman light energy may comprise one or more of fluorescent light, light having wavelengths of the monochromatic illumination beam, ambient light or other parasitic light.

An electronic excitation of the constituent may correspond to a precisely excited state of the biomarker. An electronic excitation of the constituent may be above a virtual state corresponding to Raman emission of the constituent.

The monochromatic light beam may comprise a bandwidth of no more than about ten nanometers. The monochromatic light beam may comprise a bandwidth of no more than about three nanometers.

The laser may comprise a tunable laser, wherein a bandwidth of the tunable laser may comprise bandwidth of no more than about a nanometer when tuned to a wavelength.

The wavelength separator may comprise one or more of a prism, a granting, a mirror, an etalon, an optical filter or a plurality of optical filters.

The detector may comprise one or more of a plurality of detectors or a plurality of detector elements.

The blood constituent may comprise a biomarker. The biomarker may comprise one or more of Glucose, Troponin Complex, Troponin T (TnT), Troponin I (TnI), Troponin C (TnC), a cardiac biomarker, a Troponin cardiac biomarker, a breast cancer biomarker, Breast Cancer 1 Biomarker (BRCA1), Breast Cancer 2 Biomarker (BRCA2), a biomarker related to coronary disease, B-type Natriuretic Peptide (BNP) and N-terminal proBNP (NT-proBNP), an infection specific biomarker, a biomarker related to dementia, Beta Amyloid, Low Density Lipoprotein (LDL), High Density Lipoprotein (HDL), Cholesterol, a Triglyceride, a Thyroid Stimulating Hormone (TSH), Creatine Kinase, Prostate Specific Antigen (PSA), Creatinine, Globulin, Adenovirus DNA, Alanine Aminotransferase (ALT/SGPT), Albumin, Alkaline Phosphatase (ALP), Alpha-1-Acid Glycoprotein, Alpha-1-Antitrypsin, Alpha-Fetoprotein (AFP), Amphetamines, Amylase, Androstenedione, RBC Antibody Detection, Anti-Mullerian Hormone (AMH), Antinuclear Antibodies, Apolipoprotein (apo A-1, apo B), Apolipoprotein A-1 (apo A-1), Apolipoprotein B (apo B), Aspartate Aminotransferase (AST/SGOT), B Cell, Barbiturates, Benzodiazepines, Beta-2 Microglobulin, Bilirubin, Blood Type (ABO/RhD), Blood Urea Nitrogen (BUN), Borrelia Antibody (Lyme Disease), Calcitonin, Calcium, Cancer Antigen 125 (CA 125), Cancer Antigen 15-3 (CA 15-3), Cancer Antigen 27.29 (CA 27.29), Cancer Antigen-GI (CA 19-9), Carbon Dioxide, Carcinoembryonic Antigen (CEA), Cardiolipin Antibody (ACA), CBC (Complete Blood Count), CD4, CD8, Celiac Panel, Chlamydia Trachomatis, Gonorrhea, Chloride, Cholinesterase, Cocaine, Complement Component 3 antigen, Complement Component 4 antigen, Cortisol, C-Peptide, C-Reactive Protein (CRP), Cyclic Citrullinated Peptide (CCP) Antibody, Cyclosporine A, Cystatin C, Cytomegalovirus (CMV) Antibody, Cytomegalovirus (CMV) Antibody, D-Dimer, Deamidated Gliadin Peptide (DGP) Antibody, Deamidated Gliadin Peptide (DGP) Antibody, Dehydroepiandrosterone Sulfate (DHEA-S), Deoxypyridinoline crosslinks (DPD) (Collagen crosslinks), Double-stranded DNA (dsDNA) Antibody, EBV Early D Antigen (EA-D), EBV Nuclear Antibody, EBV Viral Capsid Antigen (VCA), EBV Viral Capsid Antigen (VCA), Ecstasy (MDMA), Endomysial Antibody (EMA), Endomysial Antibody (EMA), Epstein-Barr (EBV) Antibody, Erythrocyte Sedimentation Rate (ESR/Sed Rate), Estradiol, Estriol, Estrone, Ethanol, Extractable, Ferritin, Fibrinogen, Folate (Folic acid), Follicle Stimulating Hormone (FSH), Gamma-Glutamyltransferase (GGT), Gastrin, Glucose, Growth Hormone (HGH), chronic Haptoglobin (hCG), *Helicobacter Pylori* (*H. Pylori*), Hematocrit (HCT), Hemoglobin (HGB), Hemoglobin A1c (HbA1c), Hemogram 2, Hepatitis A (HAV) Antibody, Hepatitis A (HAV) Antibody, Hepatitis B (HBV) Core Antibody, Hepatitis B (HBV) Core Antibody, Hepatitis B (HBV) Surface Antibody (HBsAb), Hepatitis B (HBV), Hepatitis C (HCV) Antibody, HER-2/neu, Herpes Simplex 1 (HSV1), Herpes Simplex 2 (HSV2), HIV-1, Homocysteine, IGF-1 (Insulin-like Growth Factor 1), Insulin, Iron, Lactate Dehydrogenase, Lead, Lipase, Lithium, Luteinizing Hormone (LH), Magnesium, Marijuana (THC), Measles, Mumps, and Rubella (MMR) Immunity, Methadone (dolophine), Methamphetamines, Microalbumin, Mumps Antibody, Myoglobin, N. Gonorrhea, Natural Killer Cells, Nuclear Antigen Antibody Jo-1, Nuclear Antigen Antibody RNP, Nuclear Antigen Antibody Sc1-70, Nuclear Antigen Antibody Sm, Nuclear Antigen Antibody SSA, Nuclear Antigen Antibody SSB, Opiates, Parathyroid Hormone (PTH), Phencyclidine (PCP), Phosphorus, Platelets, Potassium, Prealbumin, Progesterone, Prolactin, Propoxyphene, Reticulocyte Count, Rheumatoid Factor, Rubella Antibody, Rubeola (Measles) Antibody, Sex Hormone-binding Globulin (SHBG), Sodium, Streptolysin O Antibody, Treponema Pallidum Antibody, T Cell, Triiodothyronine (T3), Testosterone, Thyroglobulin, Thyroglobulin Antibodies (TAA), Thyroid Peroxidase (TPO) Antibody, Thyroxine Binding Globulin (TBG), Thyroxine (T4), Tissue Transglutaminase (tTG) Antibody, Toxoplasma, Transferrin, Treponema Pallidum Antibody, Triiodothyronine (FT3), Uric Acid, Varicella-Zoster (VZV) Antibody, Vitamin B-12, Vitamin D 25-OH, or WBC.

The light source, the reference light source, the optical delivery system, the detector and the reference detector may be configured to be worn by the subject.

The spectrometer may further comprise a support shaped to couple to a head of the subject and support the light source, the reference light source, the optical delivery system, the detector and the reference detector with the head of the subject. The support and the light source, the reference light source, the optical delivery system, the detector and the reference detector may have a weight within a range from about 150 grams to about 250 grams. The support and the light source, the reference light source, the optical delivery system, the detector and the reference detector may weigh no more than about 125 grams. The support may comprise one or more of an eyeglass frame, a helmet, goggles, or a spiral extension to wrap around a head of the subject. The support may be configured to support the processor and a power supply and wireless communication circuitry. The processor and the power supply may be located away from the light source, the reference light source, the optical delivery system, the detector and the reference detector in order to distribute weight of the support when placed on the head of the subject. The support may comprise a cover to inhibit ambient light from illuminating the region.

The spectrometer may further comprise a support configured to support the light source, the reference light source, the optical delivery system, the detector and the reference detector, wherein the support is configured for placement on a table top.

The spectrometer may further comprise a support shaped to support a chin of the subject in order to align the light source, the reference light source, the optical delivery system, the detector and the reference detector.

The support may comprise a visual illuminator visible to the user to direct a gaze of the viewer in order to align the tissue with the optical system. The visible illuminator may be located on a first side of the eye on the support and the optical system and detector may be located on a second side of the eye on the support in order to measure a conjunctiva of the eye when the subject views the visible illuminator.

The blood vessels may be part of a conjunctiva of an eye of the subject or a tympanic membrane of an ear of the subject. The epithelium may comprise an epithelium of the one or more of the conjunctiva of the eye of the subject or the tympanic membrane of the ear of the subject.

One or more of the reference beam or an additional light beam and one or more of the reference detector or another detector may be configured to measure absorption of the region. One or more of the reference beam or an additional light beam and one or more of the reference detector or another detector may be configured to measure near infrared light energy of the region. One or more of the reference beam or an additional light beam and one or more of the reference detector or another detector may be configured to measure near infrared spectra of the region.

The processor may be configured to repeatedly measure the Raman peaks and the portion with a plurality of measurements to increase a signal to noise ratio. The processor may be configured with instructions to extract data from signals from the detector and the reference detector in response to the resonance Raman peaks and the portion of the reference beam using signal processing comprising one or more of filtering, subtraction of a baseline, a Fourier transform, a wavelet transform, a partial least square regression, a differentiation, or a ratio of a signal from the detector to a ratio of a signal from the reference detector.

The reference beam may comprise a calibration beam, and the amount may be determined in response to a ratio of a resonance Raman signal from the detector to a calibration signal from the portion of the beam received with the reference detector.

The monochromatic light beam and the reference beam may be arranged in a coaxial configuration to direct the monochromatic light beam and the reference beam along a common axis toward the region. The monochromatic light beam and the reference beam may be arranged in a confocal configuration to focus the monochromatic light beam and the reference beam together on a tissue volume of the region.

The spectrometer may further comprise a camera configured with an optic to view the blood vessels of the region and align the monochromatic beam and the measurement beam with the region.

The region may comprise a volume located below the epithelium.

The portion of the reference beam backscattered from the blood at the region may comprise one or more of light having wavelengths of the reference beam, secondary radiation from the reference beam, or fluorescence from the reference beam.

The spectrometer may further comprise instructions to determine the amount of the blood constituent from the resonance Raman peaks and the portion of the reference beam backscattered from the blood at the region with one or more of a processor electrically coupled to the detector and the reference detector, a processor of a mobile computing device, or a processor of a remote server. The processor electrically coupled to the detector and the reference detector may comprise the instructions to determine the amount of the blood constituent from the resonance Raman peaks and the portion of the reference beam backscattered from the blood at the region. The processor of the mobile computing device may comprise the instructions to determine the amount of the blood constituent from the resonance Raman peaks and the portion of the reference beam backscattered from the blood at the region. The remote server may comprise the instructions to determine the amount of the blood constituent from the resonance Raman peaks and the portion of the reference beam backscattered from the blood at the region. The mobile computing device may comprise instructions to display the amount to a user of the spectrometer.

The spectrometer may further comprise a plurality of structures configured for insertion and removal from the spectrometer by a user to measure a plurality of blood constituents each having different Raman peaks and different resonance Raman excitation wavelengths. The plurality of structures may comprise one or more of a plurality of cartridges or a plurality of arms.

In another aspect, disclosed herein is a head worn spectrometer to measure a blood constituent of a subject. The head worn spectrometer comprises a light source to generate a monochromatic light beam, the monochromatic beam comprising one or more wavelengths having a frequency at an electronic excitation of the blood constituent to generate resonance Raman peaks. The head worn spectrometer further comprises an optical system to deliver the monochromatic beam through the epithelium and vessel walls to the blood constituent at the region and receive light energy from the blood constituent through the epithelium and the vessel walls. The optical system may comprise an optical wavelength separator to selectively transmit resonance the Raman peaks. The head worn spectrometer further comprises a detector coupled to the optical delivery system to measure the resonance Raman peaks from the blood constituent at the region. The head worn spectrometer further comprises a reference light source to generate a reference beam to illuminate blood at the region, and a reference detector to measure a portion of the reference beam backscattered from the blood at the region. The head worn spectrometer further comprises a support to couple to the head of the wearer and support the light source, the optical system, the detector, the reference light source and the reference detector. The head worn spectrometer further comprises a processor coupled to the light source, the reference light source, the detector and the reference detector to measure the resonance Raman peaks and the portion of backscatter from the reference beam. The head worn spectrometer may comprise a weight within a range from about 150 grams to about 250 grams.

In another aspect, disclosed herein is a method of non-invasively measuring a blood constituent through an epithelium and vessel walls of blood vessels at a region of a subject with light with a spectrometer. The method comprises generating a monochromatic light beam with a light source, the monochromatic beam comprising one or more wavelengths having a frequency at an electronic excitation of the blood constituent to generate resonance Raman peaks. The method further comprises delivering the monochromatic light beam through the epithelium vessel walls to the blood constituent at the region with an optical delivery system. The method further comprises receiving with an optical separator light energy from the blood constituent through the epithelium and the vessel walls to selectively transmit the resonance Raman peaks. The method further comprises measuring the resonance Raman peaks from the blood constituent at the region with an optical detector. The method further comprises generating a reference beam to illuminate blood at the region with the reference light beam, and measuring a portion of the reference beam backscattered from the blood at the region with a reference detector in order to determine an amount of the blood constituent from the resonance Raman peaks and the portion of the reference beam backscattered from the blood at the region.

The method may further comprise determining the amount of the blood constituent from the resonance Raman peaks and the portion of the reference beam backscattered from the blood at the region with one or more of a processor electrically coupled to the detector and the reference detector, a processor of a mobile computing device, or a processor of a remote server.

The method may further comprise placing a spectral device anterior to an eye of the subject with the eye covered to inhibit ambient light from reaching the region.

In some embodiments of the method, gaze of the subject may be directed away from a spectrometer in order to measure a conjunctiva of an eye of the subject. In some embodiments of the method, a position of the eye may be verified by one or more of a measurement beam or an operator of the spectrometer.

The region may comprise a volume of blood and the reference beam may measure a second constituent of blood, the second constituent comprising a greater amount by volume than the constituent of interest.

The processor may be coupled to the light source and configured to transmit the monochromatic light beam to the region with an amount of energy greater than the reference beam. The processor may be further configured to detect a presence of the blood vessels with the portion of the reference beam and transmit the monochromatic beam in response to the presence of the blood vessel. The amount of energy of the monochromatic beam may exceed a retina safe threshold of the measurement beam and the reference beam may not exceed a retina safe threshold of the reference beam. The processor may be configured to transmit the reference beam and not to transmit the monochromatic light beam when the presence of the blood vessels has not been detected.

The optical system may be configured to focus the monochromatic light beam on a blood vessel beneath the epithelium and the optical system may be configured to receive the resonance Raman peaks from the blood constituent through the epithelium and direct the resonance Raman peaks to the detector. The optical system may comprise a focusing element to collect the backscattered light from a region of the tissue. The focusing element may comprise one or more of a lens, an objective lens, a reflector, a curved reflector, a spherical reflector, or a curved reflector with an aperture, a concave reflector with an aperture, a convex reflector, a convex reflector aligned with an aperture of a concave reflector or Schwarzschild optics. The focusing element may be configured to receive light from the region and transmit the resonance Raman peaks in a substantially collimated configuration toward the detector.

The monochromatic light source may be transmitted toward the region in a substantially collimated configuration. The optical system may comprise an optical path along which the resonance Raman peaks and the portion are transmitted coaxially toward the detector and the reference detector.

The processor may be coupled to the reference detector and configured to determine the amount of the constituent in response to an intensity of the portion of the beam received from the tissue and an intensity of the resonance Raman peaks. The processor may be coupled to the reference detector and configured to determine a concentration of the constituent in blood in response to an intensity of the portion of the beam received from the tissue and an intensity of the resonance Raman peaks. The processor may be coupled to the reference detector and configured to determine a concentration of the constituent in response to an intensity of the portion of the beam received from the tissue and an intensity of the resonance Raman peaks, the concentration comprising the amount of the constituent per unit volume of the blood.

The wavelength separator may be configured to separate non-resonance Raman light energy from the resonance Raman peaks, wherein the non-resonance Raman light energy may comprise one or more of fluorescent light, light having wavelengths of the monochromatic illumination beam, ambient light or other parasitic light.

An electronic excitation of the constituent may correspond to a precisely excited state of the biomarker. An electronic excitation of the constituent may be above a virtual state corresponding to Raman emission of the constituent.

The monochromatic light beam may comprise a bandwidth of no more than about ten nanometers. The monochromatic light beam may comprise a bandwidth of no more than about three nanometers.

The laser may comprise a tunable laser wherein a bandwidth of the tunable laser may comprise a bandwidth of no more than about a nanometer when tuned to a wavelength.

The wavelength separator may comprise one or more of a prism, a granting, a mirror, an etalon, an optical filter or a plurality of optical filters.

The detector may comprise one or more of a plurality of detectors or a plurality of detector elements.

The blood constituent may comprise a biomarker. The biomarker may comprise one or more of Glucose, Troponin Complex, Troponin T (TnT), Troponin I (TnI), Troponin C (TnC), a cardiac biomarker, a Troponin cardiac biomarker, a breast cancer biomarker, Breast Cancer 1 Biomarker (BRCA1), Breast Cancer 2 Biomarker (BRCA2), a biomarker related to coronary disease, B-type Natriuretic Peptide (BNP) and N-terminal proBNP (NT-proBNP), an infection specific biomarker, a biomarker related to dementia, Beta Amyloid, Low Density Lipoprotein (LDL), High Density Lipoprotein (HDL), Cholesterol, a Triglyceride, a Thyroid Stimulating Hormone (TSH), Creatine Kinase, Prostate Specific Antigen (PSA), Creatinine, Globulin, Adenovirus DNA, Alanine Aminotransferase (ALT/SGPT), Albumin, Alkaline Phosphatase (ALP), Alpha-1-Acid Glycoprotein, Alpha-1-Antitrypsin, Alpha-Fetoprotein (AFP), Amphetamines, Amylase, Androstenedione, RBC Antibody Detection, Anti-Mullerian Hormone (AMH), Antinuclear Antibodies, Apolipoprotein (apo A-1, apo B), Apolipoprotein A-1 (apo A-1), Apolipoprotein B (apo B), Aspartate Aminotransferase (AST/SGOT), B Cell, Barbiturates, Benzodiazepines, Beta-2 Microglobulin, Bilirubin, Blood Type (ABO/RhD), Blood Urea Nitrogen (BUN), Borrelia Antibody (Lyme Disease), Calcitonin, Calcium, Cancer Antigen 125 (CA 125), Cancer Antigen 15-3 (CA 15-3), Cancer Antigen 27.29 (CA 27.29), Cancer Antigen-GI (CA 19-9), Carbon Dioxide, Carcinoembryonic Antigen (CEA), Cardiolipin Antibody (ACA), CBC (Complete Blood Count), CD4, CD8, Celiac Panel, Chlamydia Trachomatis, Gonorrhea, Chloride, Cholinesterase, Cocaine, Complement Component 3 antigen, Complement Component 4 antigen, Cortisol, C-Peptide, C-Reactive Protein (CRP), Cyclic Citrullinated Peptide (CCP) Antibody, Cyclosporine A, Cystatin C, Cytomegalovirus (CMV) Antibody, Cytomegalovirus (CMV) Antibody, D-Dimer, Deamidated Gliadin Peptide (DGP) Antibody, Deamidated Gliadin Peptide (DGP) Antibody, Dehydroepiandrosterone Sulfate (DHEA-S), Deoxypyridinoline crosslinks (DPD) (Collagen crosslinks), Double-stranded DNA (dsDNA) Antibody, EBV Early D Antigen (EA-D), EBV Nuclear Antibody, EBV Viral Capsid Antigen (VCA), EBV Viral Capsid Antigen (VCA), Ecstasy (MDMA), Endomysial Antibody (EMA), Endomysial Antibody (EMA), Epstein-Barr (EBV) Antibody, Erythrocyte Sedimentation Rate (ESR/Sed Rate), Estradiol, Estriol, Estrone, Ethanol, Extractable, Ferritin, Fibrinogen, Folate (Folic acid), Follicle Stimulating Hormone (FSH), Gamma-Glutamyltransferase (GGT), Gastrin, Glucose, Growth Hormone (HGH), chronic Haptoglobin (hCG), *Helicobacter Pylori* (*H. Pylori*), Hematocrit (HCT), Hemoglobin (HGB), Hemoglobin Alc (HbAlc), Hemogram 2, Hepatitis A (HAV) Antibody, Hepatitis A (HAV) Antibody, Hepatitis B (HBV) Core Antibody, Hepatitis B (HBV) Core Antibody, Hepatitis B (HBV) Surface Antibody (HBsAb), Hepatitis B (HBV), Hepatitis C (HCV) Antibody, HER-2/neu, Herpes Simplex 1 (HSV1), Herpes Simplex 2 (HSV2), HIV-1, Homocysteine, IGF-1 (Insulin-like Growth Factor 1), Insulin, Iron, Lactate Dehydrogenase, Lead, Lipase, Lithium, Luteinizing Hormone (LH), Magnesium, Marijuana (THC), Measles, Mumps, and Rubella (MMR) Immunity, Methadone (dolophine), Methamphetamines, Microalbumin, Mumps Antibody, Myoglobin, N. Gonorrhea, Natural Killer Cells, Nuclear Antigen Antibody Jo-1, Nuclear Antigen Antibody RNP, Nuclear Antigen Antibody Scl-70, Nuclear Antigen Antibody Sm, Nuclear Antigen Antibody SSA, Nuclear Antigen Antibody SSB, Opiates, Parathyroid Hormone (PTH), Phencyclidine (PCP), Phosphorus, Platelets, Potassium, Prealbumin, Progesterone, Prolactin, Propoxyphene, Reticulocyte Count, Rheumatoid Factor, Rubella Antibody, Rubeola (Measles) Antibody, Sex Hormone-binding Globulin (SHBG), Sodium, Streptolysin O Antibody, Treponema Pallidum Antibody, T Cell, Triiodothyronine (T3), Testosterone, Thyroglobulin, Thyroglobulin Antibodies (TAA), Thyroid Peroxidase (TPO) Antibody, Thyroxine Binding Globulin (TBG), Thyroxine (T4), Tissue Transglutaminase (tTG) Antibody, Toxoplasma, Transferrin, Treponema Pallidum Antibody, Triiodothyronine (FT3), Uric Acid, Varicella-Zoster (VZV) Antibody, Vitamin B-12, Vitamin D 25-OH, or WBC.

The light source, the reference light source, the optical delivery system, the detector and the reference detector may be configured to be worn by the subject.

The method may further comprise providing a support shaped to couple to a head of the subject and support the light source, the reference light source, the optical delivery system, the detector and the reference detector with the head of the subject. The support and the light source, the reference light source, the optical delivery system, the detector and the reference detector may weigh no more than about 250 grams. The support and the light source, the reference light source, the optical delivery system, the detector and the reference detector may weigh no more than about 125 grams. The support may comprise one or more of an eyeglass frame, a helmet, goggles, a spiral extension to wrap around a head of the subject. The support may be configured to support the processor and a power supply and wireless communication circuitry and the processor and the power supply may be located away from the light source, the reference light source, the optical delivery system, the detector and the reference detector in order to distribute weight of the support when placed on the head of the subject. The support may comprise a cover to inhibit ambient light from illuminating the region.

The method may further comprise providing a support configured to support the light source, the reference light source, the optical delivery system, the detector and the reference detector, wherein the support is configured for placement on a table top.

The method may further comprise providing a support shaped to support a chin of the subject in order to align the light source, the reference light source, the optical delivery system, the detector and the reference detector.

The support may comprise a visual illuminator visible to the user to direct a gaze of the viewer in order to align the tissue with the optical system. The visible illuminator may be located on a first side of the eye on the support and the optical system and detector may be located one a second side of the eye on the support in order to measure a conjunctiva of the eye when the subject views the visible illuminator.

The blood vessels may be part of a conjunctiva of an eye of the subject or a tympanic membrane of an ear of the subject. The epithelium may comprise an epithelium of the one or more of the conjunctiva of the eye of the subject or the tympanic membrane of the ear of the subject.

One or more of the reference beam or an additional light beam and one or more of the reference detector or another detector may be configured to measure absorption of the region. One or more of the reference beam or an additional light beam and one or more of the reference detector or another detector may be configured to measure near infrared light energy of the region. One or more of the reference beam or an additional light beam and one or more of the reference detector or another detector may be configured to measure near infrared spectra of the region.

The processor may be configured to repeatedly measure the Raman peaks and the portion with a plurality of measurements to increase a signal to noise ratio.

The processor may be configured with instructions to extract data from signals from the detector and the reference detector in response to the resonance Raman peaks and the portion of the reference beam using signal processing comprising one or more of filtering, subtraction of a baseline, a Fourier transform, a wavelet transform, a partial least square regression, a differentiation, or a ratio of a signal from the detector to a ratio of a signal from the reference detector.

The reference beam may comprise a calibration beam wherein the amount may be determined in response to a ratio of a resonance Raman signal from the detector to a calibration signal from the portion of the beam received with the reference detector.

The monochromatic light beam and the reference beam may be arranged in a coaxial configuration to direct the monochromatic light beam and the reference beam along a common axis toward the region. The monochromatic light beam and the reference beam may be arranged in a confocal configuration to focus the monochromatic light beam and the reference beam together on a tissue volume of the region.

The method may further comprise providing a camera configured with an optic to view the blood vessels of the region and align the monochromatic beam and the measurement beam with the region.

The region may comprise a volume located below the epithelium.

The portion of the reference beam backscattered from the blood at the region may comprise one or more of light having wavelengths of the reference beam, secondary radiation from the reference beam, or fluorescence from the reference beam.

The method may further comprise providing instructions to determine the amount of the blood constituent from the resonance Raman peaks and the portion of the reference beam backscattered from the blood at the region with one or more of a processor electrically coupled to the detector and the reference detector, a processor of a mobile computing device, or a processor of a remote server. The processor electrically coupled to the detector and the reference detector may comprise the instructions to determine the amount of the blood constituent from the resonance Raman peaks and the portion of the reference beam backscattered from the blood at the region. The processor of the mobile computing device may comprise the instructions to determine the amount of the blood constituent from the resonance Raman peaks and the portion of the reference beam backscattered from the blood at the region. The remote server may comprise the instructions to determine the amount of the blood constituent from the resonance Raman peaks and the portion of the reference beam backscattered from the blood at the region. The mobile computing device may comprise instructions to display the amount to a user of the spectrometer.

The method may further comprise providing a plurality of structures configured for insertion and removal from the spectrometer by a user to measure a plurality of blood constituents each having different Raman peaks and different resonance Raman excitation wavelengths. The plurality of structures may comprise one or more of a plurality of cartridges or a plurality of arms.

In another aspect, disclosed herein is a spectrometer to non-invasively measure a blood constituent through an epithelium and vessel walls of blood vessels at a region of a subject with light. The spectrometer comprises a light source to generate a measurement light beam to measure the constituent, and an optical system to deliver the measurement light beam through the epithelium and vessel walls to the blood constituent at the region and receive light energy from the blood constituent through the epithelium and the vessel walls. The optical system may comprise an optical wavelength separator to selectively transmit light from the region. The spectrometer further comprises a detector coupled to the optical delivery system to measure the selectively transmitted light from the region, a reference light source to generate a reference beam to illuminate blood at the region, a reference detector to measure a portion of the reference beam backscattered from the region, and a processor coupled to the detector and the reference detector. The processor may be configured with instructions to measure the resonance Raman peaks and the portion in order to determine an amount of the blood constituent from the selectively transmitted light at the region and the portion of the reference beam backscattered from the region.

In another aspect, disclosed herein is a spectrometer to non-invasively measure a constituent of one or more of a tissue or a fluid of a subject with light. The spectrometer comprises a light source to generate a measurement light beam to measure the constituent at a region where the constituent is located. The spectrometer further comprises an optical system to deliver the measurement light beam to the constituent at the region and receive light energy from the constituent, the optical system comprising an optical wavelength separator to selectively transmit light from the region. The spectrometer further comprises a detector coupled to the optical delivery system to measure the selectively transmitted light from the region. The spectrometer further comprises a reference light source to generate a reference beam to illuminate the region, a reference detector to measure a portion of the reference beam backscattered from the region, and a processor coupled to the detector and the reference detector. The processor may be configured with instructions to measure the resonance Raman peaks and the portion in order to determine an amount of the constituent from the selectively transmitted light at the region and the portion of the reference beam backscattered from the region.

In any embodiment of a spectrometer or a method disclosed herein, the processor may be configured to output the amount on a display coupled to the processor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
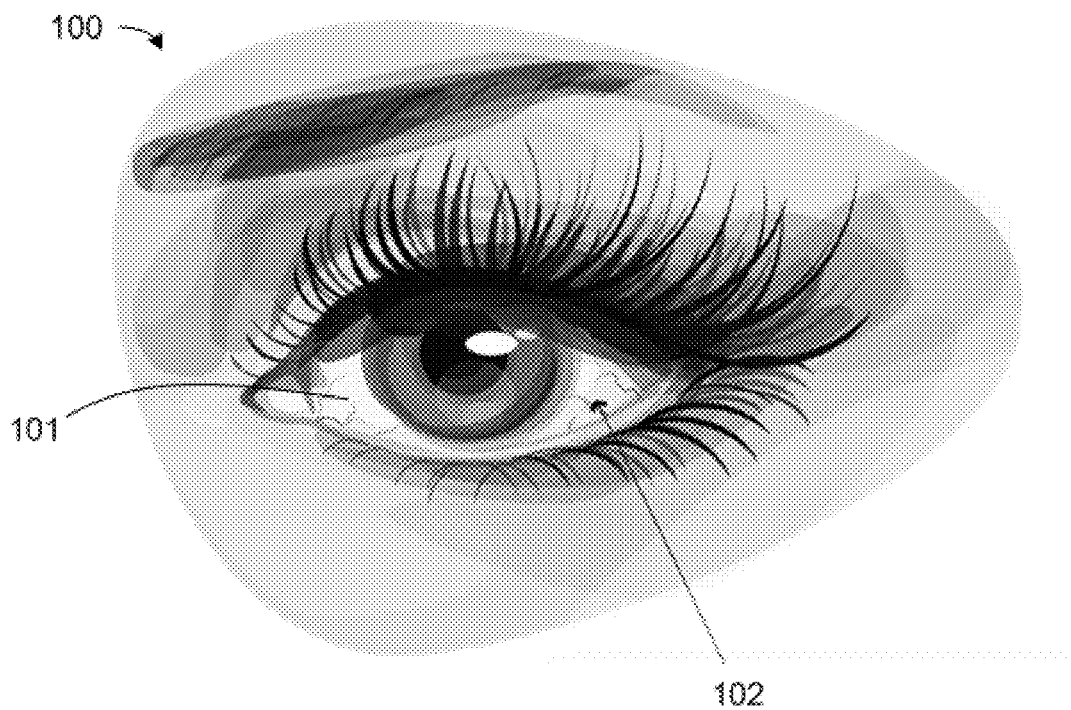
FIG. 1A shows an image of an eye highlighting the vessels of the conjunctiva, in accordance with embodiments.

In the following detailed description, reference is made to the accompanying figures, which form a part hereof. In the figures, like characters identify like elements, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. The disclosed embodiments and configurations with respect to blood shall be considered non-limiting examples, and the spectrometer and apparatus and methods disclosed herein can be configured and used to measure any of the materials disclosed herein.

As used herein, the term biomarker encompasses any measurable substance in an organism whose presence is indicative of some phenomenon, which comprises of, for example, one or more of a biological molecule, a molecule, a disease biomarker, or a blood constituent.

As used herein light encompasses electromagnetic energy having wavelengths in one or more of the ultraviolet, visible, near infrared or infrared regions of the electromagnetic energy spectrum.

The methods and spectrometer apparatus disclosed herein can be used to measure one or more of many constituents as described herein non-invasively from one or more of many types of materials of subject, such as one or more of tissue, bodily fluids, sweat, saliva, tear from the eye, conjunctival tissue, tympanic membrane tissue ("eardrum tissue"), blood, or blood vessels, for example. Although reference is made to measuring constituents from blood, a person of ordinary skill in the art can readily configure the methods and apparatus disclosed herein to measure a constituent of any of these materials in accordance of the present disclosure.

Blood is an important connective tissue embryologically having the same origin (mesodermal) as other connective tissue types, and blood also connects the body systems together bringing the needed oxygen, nutrients, hormones and other signaling molecules, and removing the wastes. Blood is also a fluid which readily flows through the body. Blood is provided as an exemplary fluid and tissue well suited for measurement in accordance with the present disclosure.

The present disclosure describes methods and apparatus to measure blood in vivo and non-invasively with high specificity. For example, cardiac Troponin I (cTnI), a biomarker of myocardial infarction, can be distinguished from other blood constituents using Raman signals, for example using resonance Raman spectroscopy. The method and apparatus can be configured to analyze the blood in the blood carrying vessels, such as capillaries of the conjunctiva. The methods and apparatus can be configured to apply resonance Raman (or any other back scattered light) spectroscopy, reflective optics (such as Schwarzschild), optical filters, detectors and signal processing techniques in order to provide accurate measurements. A second light source and detector can use the same optics to use spectroscopy methods to determine the amount of blood prior and/or during the resonance Raman measurement. This information is then used for preventing unwanted irradiance of the retina and for calibration, for example.

In many embodiments, the spectrometer system is configured for in vivo, non-invasive resonance Raman (and elastic and inelastic light back-scattering including resonance Raman) measurements in the blood vessels of the conjunctiva to detect and determine the concentration of blood constituents.

A spectrometer system can also be configured for in vivo, non-invasive absorption measurements in the blood vessels of the conjunctiva to detect and determine the concentration of blood constituents with a second measurement beam, for example.

The spectrometer systems disclosed herein can be configured in many ways may include LEDs, laser diodes, Schwarzschild reflective optics, using hemoglobin/albumin and other "stable blood constituents" as reference, measuring more than one spectral peak per excitation, protection mechanisms to protect against over exposure of the eye, alignment mechanism, handheld device, measurement of multiple biomarkers with different resonance excitation wavelength, signal extraction and processing techniques.

The spectrometer apparatus and methods as described herein can be used for non-invasive detection and monitoring of low concentrations of biomarkers and other blood constituents from systemic (in vivo) blood. The methods and apparatus may use principles of a variety of spectroscopies, including resonance, or near resonance Raman, detecting low concentrations of biomarkers such as cardiac Troponin I (cTnI) and blood constituents such as glucose based on their spectral signatures. The optical access to circulatory blood can be determined in the bulbar conjunctiva (blood vessels and capillaries in the corner of eye). A narrowly specialized spectral detector can be mounted on a head or spectacle frame or in a handheld/tabletop unit together with a safety mechanism (to prevent the iris, pupil or retina from exposure to the excitation light) and an eye positioning system. The eye positioning system can determine and guide manually or automatically the position of the eye. When the eye is in the proper specified position for acquiring the spectral signature one excitation light source can be triggered to ensure proper positioning and to acquire a signal indicative of the amount of blood (calibration). Parallel to or subsequently another light source with a wavelength that will result in the highest spectral response signal for a particular biomarker may be triggered (for example where cTnI Raman absorption peak is and Raman detector is configured to be sensitive only in the wavelength of cTnI Raman signature). The specialized spectrometer is preferably constructed with reflective optics for back-scattered light collection using Schwarzschild optical geometry. The Schwarzschild optical geometry comprises a concave reflector and a convex reflector concentrically arranged to decrease the size of the focusing element. The signals are acquired and processed for analysis. For calibration purposes the amplitude of the spectral responses of the blood constituents under consideration can be compared with the amplitude of the spectral response of stable blood constituent (e.g. hemoglobin or albumin), for example with a processor. The use of reflective optics such as Schwarzschild optics may result in achromatic light collection and optical signals, so as to allow achievement of a high numerical aperture, and decreased optical absorption losses. The numerical aperture of the optics may be within a range from about 0.2 to about 0.7, for example within a range from about 0.2 to about 0.6.

The methods and apparatus disclosed herein relate to the non-invasive detection, identification, and measurement of blood constituent concentrations for diagnostic and/or monitoring purposes. Such tissue constituents may comprise one or more of Glucose, Troponin Complex, Troponin T (TnT), Troponin I (TnI), Troponin C (TnC), a cardiac biomarker, a Troponin cardiac biomarker, a breast cancer biomarker, Breast Cancer 1 Biomarker (BRCA1), Breast Cancer 2 Biomarker (BRCA2), a biomarker related to coronary disease, B-type Natriuretic Peptide (BNP) and N-terminal proBNP (NT-proBNP), an infection specific biomarker, a biomarker related to dementia, Beta Amyloid, Low Density Lipoprotein (LDL), High Density Lipoprotein (HDL), Cholesterol, a Triglyceride, a Thyroid Stimulating Hormone (TSH), Creatine Kinase, Prostate Specific Antigen (PSA), Creatinine, Globulin, Adenovirus DNA, Alanine Aminotransferase (ALT/SGPT), Albumin, Alkaline Phosphatase (ALP), Alpha-1-Acid Glycoprotein, Alpha-1-Antitrypsin, Alpha-Fetoprotein (AFP), Amphetamines, Amylase, Androstenedione, RBC Antibody Detection, Anti-Mullerian Hormone (AMH), Antinuclear Antibodies, Apolipoprotein (apo A-1, apo B), Apolipoprotein A-1 (apo A-1), Apolipoprotein B (apo B), Aspartate Aminotransferase (AST/SGOT), B Cell, Barbiturates, Benzodiazepines, Beta-2 Microglobulin, Bilirubin, Blood Type (ABO/RhD), Blood Urea Nitrogen (BUN), Borrelia Antibody (Lyme Disease), Calcitonin, Calcium, Cancer Antigen 125 (CA 125), Cancer Antigen 15-3 (CA 15-3), Cancer Antigen 27.29 (CA 27.29), Cancer Antigen-GI (CA 19-9), Carbon Dioxide, Carcinoembryonic Antigen (CEA), Cardiolipin Antibody (ACA), CBC (Complete Blood Count), CD4, CD8, Celiac Panel, Chlamydia Trachomatis, Gonorrhea, Chloride, Cholinesterase, Cocaine, Complement Component 3 antigen, Complement Component 4 antigen, Cortisol, C-Peptide, C-Reactive Protein (CRP), Cyclic Citrullinated Peptide (CCP) Antibody, Cyclosporine A, Cystatin C, Cytomegalovirus (CMV) Antibody, Cytomegalovirus (CMV) Antibody, D-Dimer, Deamidated Gliadin Peptide (DGP) Antibody, Deamidated Gliadin Peptide (DGP) Antibody, Dehydroepiandrosterone Sulfate (DHEA-S), Deoxypyridinoline crosslinks (DPD) (Collagen crosslinks), Double-stranded DNA (dsDNA) Antibody, EBV Early D Antigen (EA-D), EBV Nuclear Antibody, EBV Viral Capsid Antigen (VCA), EBV Viral Capsid Antigen (VCA), Ecstasy (MDMA), Endomysial Antibody (EMA), Endomysial Antibody (EMA), Epstein-Barr (EBV) Antibody, Erythrocyte Sedimentation Rate (ESR/Sed Rate), Estradiol, Estriol, Estrone, Ethanol, Extractable, Ferritin, Fibrinogen, Folate (Folic acid), Follicle Stimulating Hormone (FSH), Gamma-Glutamyltransferase (GGT), Gastrin, Glucose, Growth Hormone (HGH), chronic Haptoglobin (hCG), *Helicobacter Pylori* (*H. Pylori*), Hematocrit (HCT), Hemoglobin (HGB), Hemoglobin Alc (HbAlc), Hemogram 2, Hepatitis A (HAV) Antibody, Hepatitis A (HAV) Antibody, Hepatitis B (HBV) Core Antibody, Hepatitis B (HBV) Core Antibody, Hepatitis B (HBV) Surface Antibody (HBsAb), Hepatitis B (HBV), Hepatitis C (HCV) Antibody, HER-2/neu, Herpes Simplex 1 (HSV1), Herpes Simplex 2 (HSV2), HIV-1, Homocysteine, IGF-1 (Insulin-like Growth Factor 1), Insulin, Iron, Lactate Dehydrogenase, Lead, Lipase, Lithium, Luteinizing Hormone (LH), Magnesium, Marijuana (THC), Measles, Mumps, and Rubella (MMR) Immunity, Methadone (dolophine), Methamphetamines, Microalbumin, Mumps Antibody, Myoglobin, N. Gonorrhea, Natural Killer Cells, Nuclear Antigen Antibody Jo-1, Nuclear Antigen Antibody RNP, Nuclear Antigen Antibody Scl-70, Nuclear Antigen Antibody Sm, Nuclear Antigen Antibody SSA, Nuclear Antigen Antibody SSB, Opiates, Parathyroid Hormone (PTH), Phencyclidine (PCP), Phosphorus, Platelets, Potassium, Prealbumin, Progesterone, Prolactin, Propoxyphene, Reticulocyte Count, Rheumatoid Factor, Rubella Antibody, Rubeola (Measles) Antibody, Sex Hormone-binding Globulin (SHBG), Sodium, Streptolysin O Antibody, Treponema Pallidum Antibody, T Cell, Triiodothyronine (T3), Testosterone, Thyroglobulin, Thyroglobulin Antibodies (TAA), Thyroid Peroxidase (TPO) Antibody, Thyroxine Binding Globulin (TBG), Thyroxine (T4), Tissue Transglutaminase (tTG) Antibody, Toxoplasma, Transferrin, Treponema Pallidum Antibody, Triiodothyronine (FT3), Uric Acid, Varicella-Zoster (VZV) Antibody, Vitamin B-12, Vitamin D 25-OH, or WBC, for example.

A person of ordinary skill in the art can conduct experiments to identify a constituent suitable for resonance Raman measurements and configure the monochromatic light source and optical wavelength separator and detector in accordance with the teachings of the present disclosure.

Although specific reference is made to detection of a blood constituent at the blood vessels of the conjunctiva of the eye, the methods and apparatus disclosed herein can be used in many tissues comprising an epithelium. For example, the methods and apparatus disclosed herein can be used at any location on or within the human body which generates scatter in response to illumination by a light source. For example, the embodiments disclosed herein may be used to detect and/or measure a blood constituent at the retina or tympanic membrane, for example.

FIG. 1A shows an image of an eye 100 highlighting the blood vessels 102 of the conjunctiva 101. The eye 100 as a diagnostic site allows for non-invasive in vivo analysis of blood constituents, for example biomarkers, quickly and safely. The blood vessels in one or more of the retina or the conjunctiva of the eye may be assessed using a variety of imaging techniques as described herein to detect, identify, and determine the concentration of blood constituents for diagnosis and monitoring purposes. The bulbar conjunctiva 101 of an eye comprises an epithelium covering a stromal layer comprising a network of blood-carrying vessels and capillaries 102 anterior to the sclera of the eye. Unlike the retina, which has a number of intraocular components (including the cornea, anterior chamber, lens, and vitreous humor) which may alter, obscure, or impair the transmission of light between it and an external light source, the blood vessels 102 of the conjunctiva 101 may be nearly directly accessible by an external light source and may therefore be an advantageous diagnostic site in at least some instances. The conjunctiva may allow for greater amounts of light energy to be used than the retina, which may provide an increased signal to noise ratio and better control of the light beam to the illuminated region. However, when the lens is inadvertently placed front of the retina, the irradiance to the retina may be greater than would be ideal, which may present potential risk to the retina from the light source. The use of the reference beam as described herein can inhibit inadvertent exposure of the retina. Although the retina can be measured in accordance with embodiments, the conjunctiva 101 is less sensitive to the intensity of the light source than the retina and may therefore be chosen as a diagnostic site where safety is of concern, for example with use of high intensity or high energy light sources which may be damaging to tissue. Similar to the conjunctiva 101, the tympanic membrane of the ear also allows for superficial access to blood vessels and capillaries. Alternatively or in combination, any tissue on or within the human body may be used as a diagnostic site if the scatter (i.e. scatter caused by the interaction of the light beam with the tissue) generated in tissue between the blood and the light sensor is minimal. In many embodiments, the apparatus described herein may be configured to be a head-worn device, for example a pair of spectacles. In such instances, the conjunctiva 101 may be advantageous as a diagnostic site in that the light source and optics of the device may be positioned so as to not obscure the field of view of the wearer (e.g. the patient) and thereby allow for use during normal daily activities.

Figure 1B:
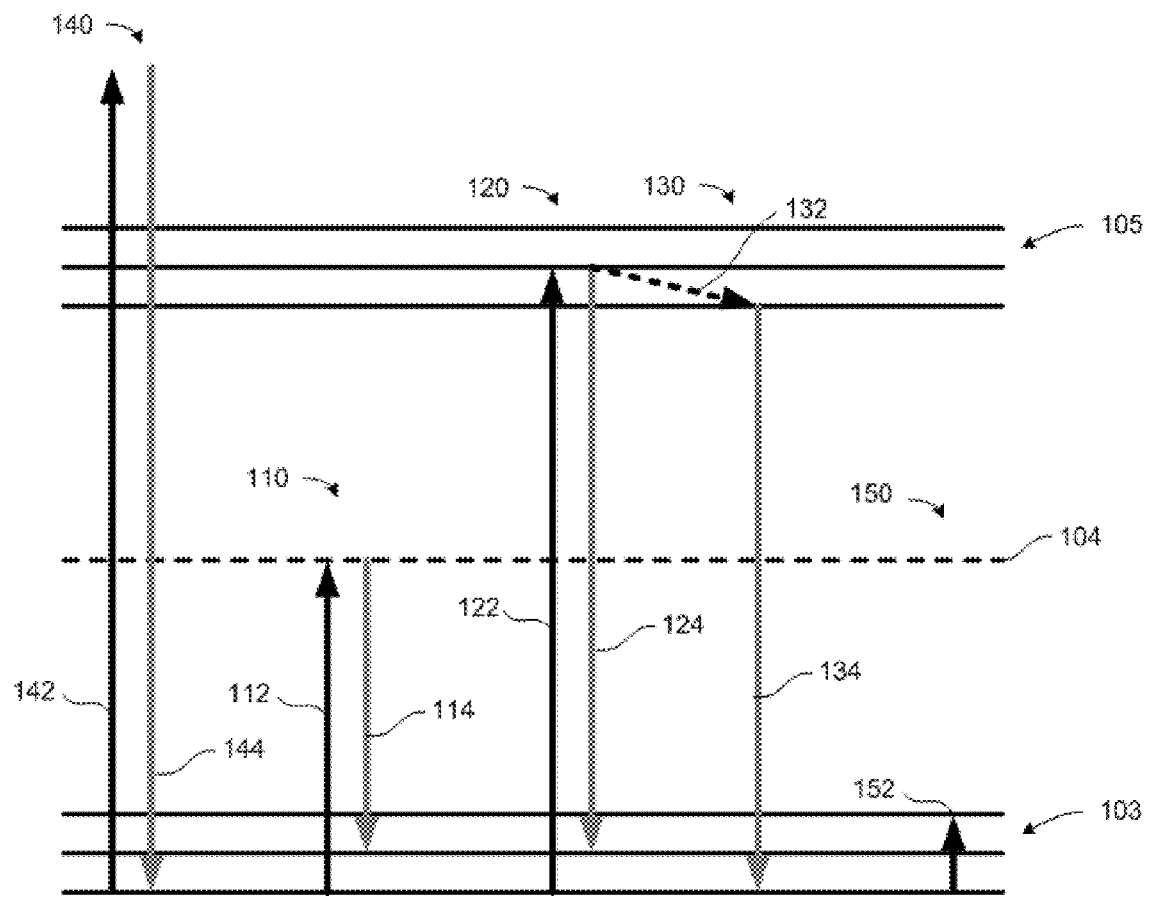
FIG. 1B shows an diagram illustrating the difference between resonance Raman spectroscopy and other non-resonance Raman spectroscopies, in accordance with embodiments.

FIG. 1B shows a diagram illustrating the difference between resonance Raman spectroscopy and non-resonance Raman spectroscopy, both of which are suitable for incorporation in accordance with the present disclosure. Resonance Raman spectroscopy is one technique of many which may be suitable for use with the methods and apparatus described herein. Raman spectroscopy is based on the inelastic scattering of optical radiation and can be used to observe vibrational or rotational changes in a molecule or system of interest, for example a biomarker. When a sample is illuminated by a light source, the backscattered light may comprise Rayleigh scattering 140, fluorescence 130, Raman scattering 110, and resonance Raman induced scattering 120. Interaction between the radiation and the sample may result in changes in the excitation of state of the sample electrons, exciting the electrons from a stable ground state 103 to an unstable virtual state 104. The instability of the virtual state 104 results in light scattering from the sample as the electrons return to a stable ground state 103.

Elastic scattering, or Rayleigh scattering 140, occurs when the radiation is scattered at the wavelength corresponding to the incident light beam. The electrons of the sample are excited 142 to an unstable virtual state 104 and radiation is emitted 144 at the same frequency and wavelength as the incident light beam as the electrons return to their original ground energy state 103. The majority of the light scattered by a sample may comprise Rayleigh scattering.

Inelastic scattering, or Raman scattering 110, occurs when the radiation is scattered at a frequency different from the incident light beam. The electrons of the sample are excited 112 to an unstable virtual state 104 and radiation is emitted 114 at the a different frequency and wavelength as the incident light beam as the electrons are polarized by the radiation such that they return to a ground energy state 103 with a slightly different energy level (e.g. a different rotational or vibrational state). The resulting shifts in frequency may be measured for a given sample to provide a fingerprint by which the molecules of the sample may be identified.

Resonance Raman spectroscopy 120 differs from non-resonant Raman spectroscopy 110 in that it exploits information about the electronic transition of a sample. Use of a light source with a frequency at or near the frequency of the electronic transition of the sample provides the electrons with enough energy to be excited 122 to a higher electronic state 105. When the electrons transition 124 back to the ground state 103, the intensity of the scattered light is greatly enhanced compared to non-resonance Raman scattering 110. Resonance Raman spectroscopy 120 has more energy and is therefore much more sensitive than non-resonance Raman spectroscopy 110 and may be used to analyze samples with concentrations as low as $10^{-8}$ M (molar) whereas non-resonance Raman can analyze samples with concentrations no lower than 0.1 M in some instances.

Fluorescence 130 may occur when the radiation of the incident light is absorbed by fluorophores within the sample and radiation of a lower energy light is emitted by the sample. A light source may be used to excite 122 an electron from a ground energy state 103 and transition from a higher energy 105. Energy may be absorbed 132 by the electron before being emitted at a lower energy state as the electron transitions 134 back to its original ground energy state 103. Fluorescence is more likely to be induced even in a non-fluorescent molecule during resonance Raman spectroscopy than non-resonance Raman spectroscopy because it uses light sources at frequencies near that of a molecule's electronic transition. Fluorescence interference may represent a challenge to resonance Raman spectroscopy and may be addressed with optical filters, signal processing, and/or excitation light source optimization.

When a near infrared (NIR) or infrared (IR) light source is used, the backscattered light may further contain information about the IR absorption 150 of the sample. By comparing the amount of radiation provided to the sample with the amount of radiation backscattered from the sample, the amount of radiation absorbed 152 by the sample may be determined. Similar to Raman and resonance Raman spectroscopies, IR spectroscopy provides information about changes in the vibrational state of a molecule and may be used to identify specific samples. IR absorbance spectroscopy and Raman spectroscopy often provide complimentary and non-overlapping information about the identity of a sample and may be used separately or in combination depending on the sample or biomarker to be identified.

Resonance Raman spectroscopy, IR absorption spectroscopy, and other spectral detection techniques can be used in accordance with the methods and apparatus described herein.

Figure 2:
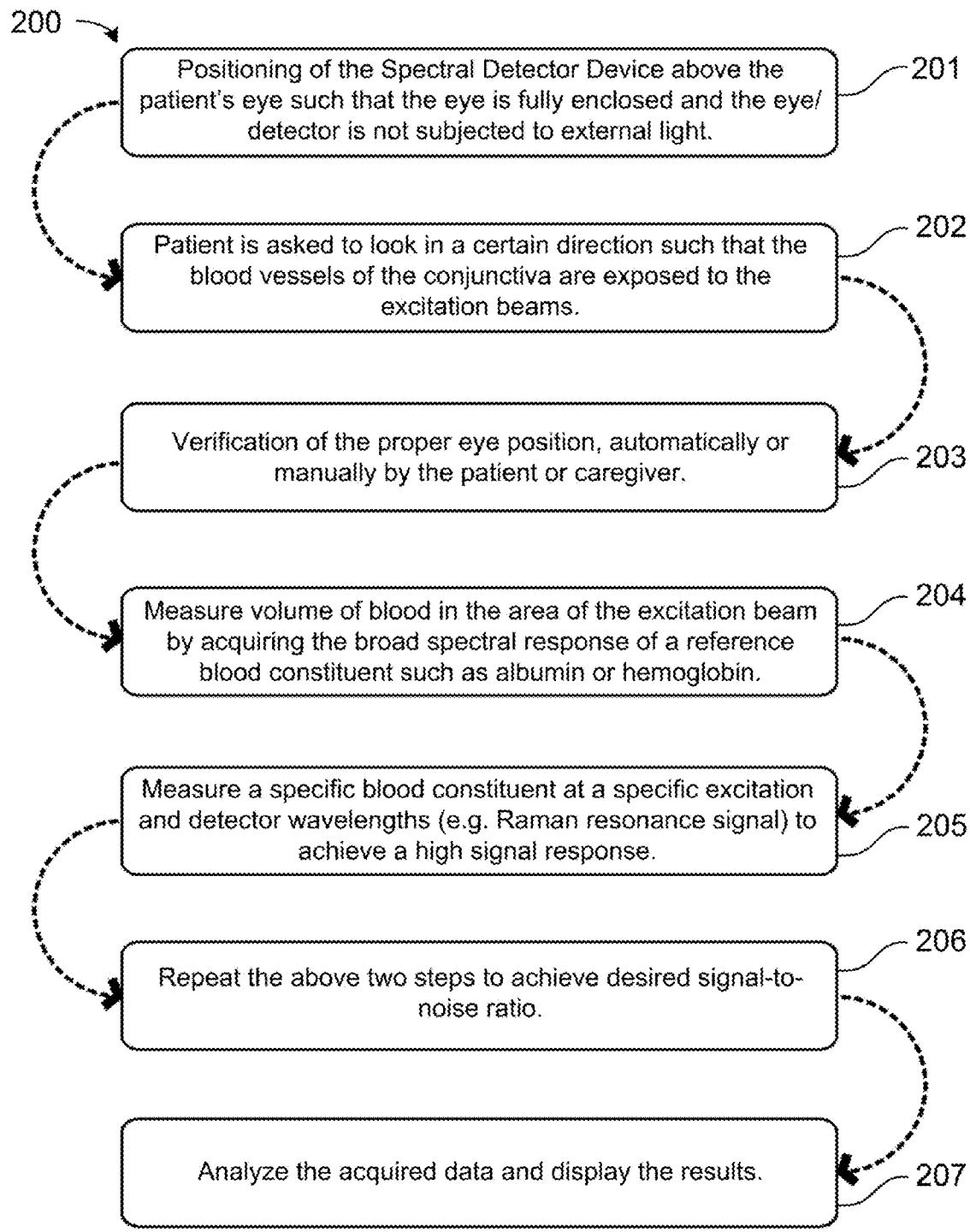
FIG. 2 shows a flow chart of a method for non-invasive detection of one or more tissue constituents, in accordance with embodiments.

FIG. 2 shows a flow chart of a method 200 for non-invasive detection of one or more tissue constituents in the blood of a patient.

At Step 201, a non-invasive spectral detector device or spectrometer may be positioned above or in front of a patient's eye. The device may be positioned such that the eye is fully enclosed by the device, for example within a cover of the device to block ambient external light from reaching the eye. The device, comprising one or more of a diagnostic first light source, a reference second light source, a diagnostic first detector, or a reference second detector, may be positioned within the enclosure so as to prevent exposure to and interference by external light. The device may for example be configured to be handheld, mounted on a spectacle frame, attached to the head, or a tabletop apparatus. The cover of the device may be used to easily, conveniently, and/or consistently position the device proximal to a patient's eye.

At Step 202, the patient may be directed to look in a specified direction so as to move the eye and expose the blood vessels of the conjunctiva. The eye may be properly positioned such that the blood vessels of the conjunctiva are exposed to an excitation light beam of the device perpendicularly at a desired region. The excitation region may comprise a volume, for example located below the epithelium of the conjunctiva. The excitation region may comprise a volume of blood, for example a volume of blood within a blood vessel beneath the epithelium of the conjunctiva.

At Step 203, the position of the eye in the proper eye position may be verified. Verification of the proper eye position may be done manually by the operator or caregiver. Alternatively or in combination, the proper eye position may be verified automatically, for example by an eye-positioning or guidance system as described further herein.

At Step 204, the device may be activated so as to measure the volume of blood in one or more of the exposed blood vessels of the conjunctiva. Measurement of blood volume may comprise emission of a light beam from a secondary light source and detection of backscattered light from the blood vessels of the conjunctiva by a secondary detector. The amount of blood may be measured so as to confirm that the eye is in the proper eye position, for example to confirm the presence of one or more blood vessels at the focal point of the light beam of the device. Confirmation of the presence of blood vessels may be used to provide additional safety or comfort of the wearer and prevent further device activity if there are no blood vessels present, for example if the eye has moved from the proper eye position. Alternatively or in combination, the amount of blood may be measured and used as a reference measurement for determining the concentration of a desired blood constituent or biomarker. The blood volume may, for example, be measured by broad spectral analysis of a common, stable, reference blood constituent, for example albumin or hemoglobin. The spectral response of the stable reference blood constituent may be correlated to expected concentrations in order to determine the volume of blood being analyzed. The concentration of other blood constituents may be determined with reference to the measured blood volume. The reference blood constituent may comprise a greater amount by volume than another blood constituent or biomarker of interest.

At Step 205, the concentration of another blood constituent, for example a biomarker, may be measured. The measurement of biomarker concentration may occur during or immediately after (e.g. faster than the eye can move) measurement of the reference blood volume. Measurement of biomarker concentration may comprise emission of a light beam from a primary light source and detection of backscattered light from the blood vessels of the conjunctiva by a primary detector. The measured biomarker may for example comprise cardiac Troponin I (cTnI) or glucose. The primary light source may for example emit a light beam comprising one or more wavelengths having a frequency at or near the frequency of an electronic transition or excitation of the biomarker in order to generate resonance. The excitation wavelength(s) of the primary light source may be chosen such that resonance occurs and the characteristic spectral response from the biomarker has sufficient amplitude to be isolated from other blood constituents, for example about maximal. The primary detector may be configured to receive the resonance Raman peaks. In some embodiments, the primary detector may be configured to receive one resonance Raman peak. In some embodiments, the primary detector may be configured to receive more than one resonance Raman peak, for example two or more resonance Raman peaks. It will be understood that many biomarkers may have more than one characteristic resonance Raman peak and the detector may therefore be configured to detect as many resonance Raman peaks as necessary to increase the specificity of biomarker identification.

Figure 5:
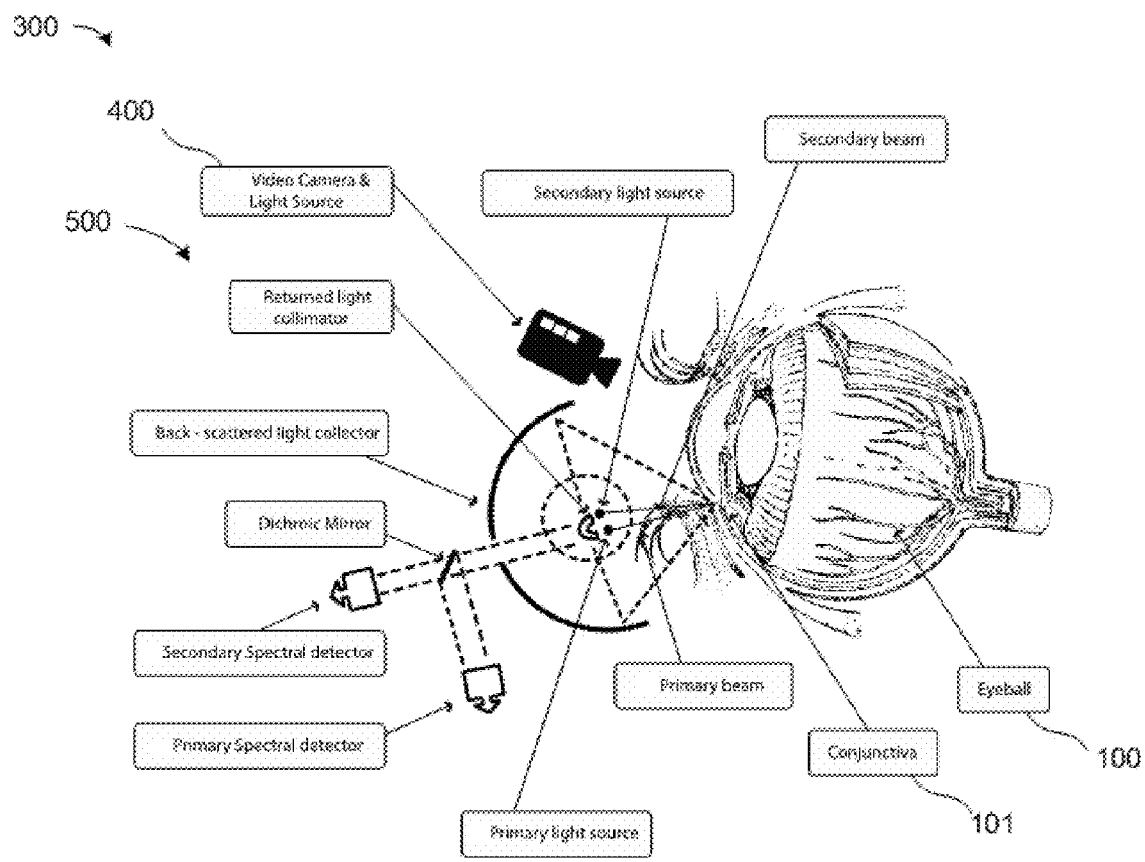
FIG. 5 shows a schematic diagram of a non-invasive spectral detection system, in accordance with embodiments.
Figure 8:
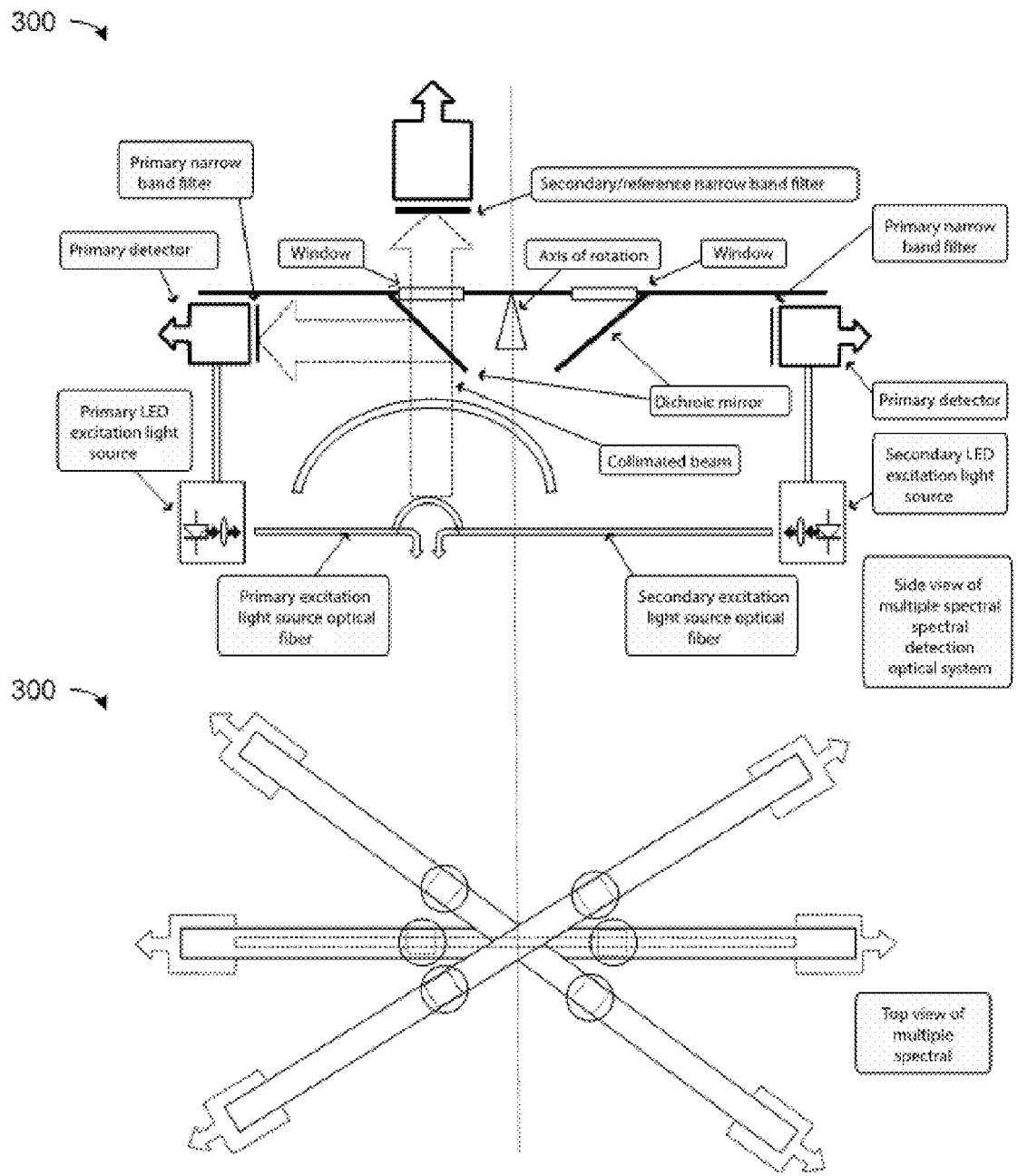
FIG. 8 shows a schematic diagram of a non-invasive spectral detection system for detection of multiple tissue constituents, in accordance with embodiments.

At Step 206, Steps 204 and 205 may be repeated so as to improve the signal-to-noise ratio of the spectral response detected for easier and more reliable analysis. Repeated monitoring of the biomarker and reference blood constituent may provide increased reliability and reduced false-positives. Alternatively or in combination, Steps 204 and 205 may be repeated so as to analyze more than one biomarker. An exemplary embodiment of a spectral detector device configured to detect a single specific blood constituent or biomarker is shown in FIG. 5. An exemplary embodiment of a spectral detector device configured to detect more than one biomarker in a patient is shown in FIG. 8. For each biomarker analyzed, a reference blood volume measurement and at least one biomarker measurement may be taken so as to determine the concentration of each biomarker in the blood. Step 206 may be repeated as many times as necessary so as to get sufficient signal amplitude and accuracy.

At Step 207, the reference blood volume data and biomarker concentration may be analyzed and the results may be displayed to the operator or caregiver. The primary and secondary detectors may be coupled to a processor to process the reference signal and the biomarker resonance Raman signal and determine therefrom the concentration of the biomarker in the blood. Signal processing methods which may be used to extract data from the acquired signal include, but are not limited to, one or more of filtering, subtraction of a baseline, Fourier transform, wavelet transform, partial least square regression, differentiation, or a ratio of the biomarker signal to reference signal. The amount of the biomarker may for example be determined in response to the ratio of the biomarker signal to the reference or calibration signal.

The processor may be configured to detect or monitor the presence or absence of blood vessels as in Step 204 prior to or during excitation of the biomarker and alter the transmission of the primary and secondary light beams by the primary and secondary light sources in response to the presence or absence of blood vessels. For example, the processor may be configured to activate or transmit the secondary light beam and not activate or transmit the primary light beam when the presence of blood vessels has not been detected.

Although the above steps show method 200 of non-invasively measuring a biomarker in the blood of a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as desired to measure one or more biomarkers. One or more of the steps of method 200 may be performed with the spectral detection apparatus as described herein.

Figure 3:
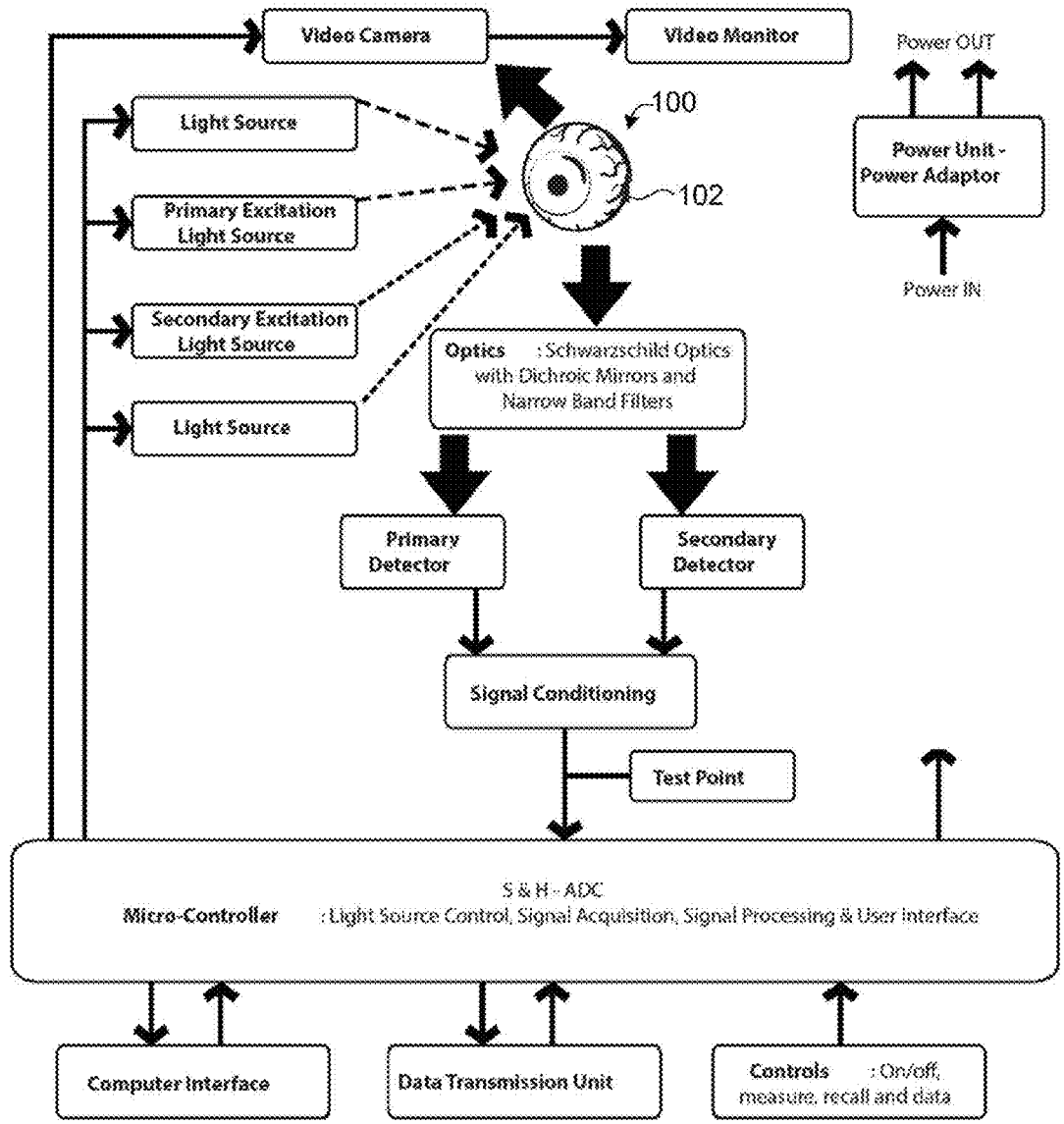
FIG. 3 shows a schematic diagram of a non-invasive spectral detector, in accordance with embodiments.

FIG. 3 shows a schematic diagram of an embodiment of a non-invasive spectral detector device 300. The detector 300 may comprise a specialized spectrometer. The spectrometer 300 may be placed anterior to the eye of a patient. The detector 300 may comprise one or more subsystems.

The detector 300 may for example comprise one or more of a video camera, a video monitor, one or more light sources for positioning the eye, a primary excitation light source, a secondary excitation light source, backscatter collecting optics, a primary light detector, a secondary light detector, one or more analog signal conditioning circuits, a micro-controller or processor, a display unit, a computer interface controller, a data transmission unit, a power unit, or a user input control unit.

The eye may be positioned at the proper eye position prior to excitation of the blood vessels for reference blood volume and biomarker concentration as previously described herein. Positioning the eye may for example be accomplished using one or more light source (for example two positioning light sources as shown in FIG. 3), a video camera, and a video monitor. A first positioning light source may for example comprise a visible light source, for example a broad spectrum light source such as a lamp, which may illuminate the eye to allow the video camera to capture images of the eye during positioning. The patient may for example be asked to look in a desired direction or at a particular point in space in order to properly position the eye for imaging. An optional second positioning light source may for example project a light beam at a spot beyond the eye, for example below the ridge of the nose, in order to guide the gaze of the patient such that the eye is moved into the proper eye position. The video signal may for example be shown on a monitor and used by a caregiver or other user to determine if the patient's conjunctival blood vessels are in the proper eye position. The video signal may for example be used to ensure that other parts of the eye, for example the iris or pupil, will not be exposed to the excitation light sources. The first and second positioning light sources may be turned off during excitation of the blood vessels so as to minimize interference of the excitation light sources and detection of the backscattered signals.

In some embodiments, the video camera and monitor may be replaced with a commercially available eye gaze tracking system. In some embodiments, the video camera may be replaced by a broadband photodiode and the light source may for example be an infrared light emitting diode (IR-LED). Light in the IR spectrum has different reflectance and absorbance properties at different locations in the eye, with the iris, pupil, and conjunctiva (and sclera) having differing properties. These differences may be used to determine the position of the eye, for example the position of the iris or pupil.

Alternatively or in combination, the device 300 may be configured so as to allow for direct visual verification of the proper eye position, as well as the position of the device with respect to the eye, by a caregiver or other operator. When direct visualization of the eye position is enabled, the use of a video system or other automated positioning system may be optional.

After the eye has been positioned and the blood vessels of the conjunctiva have been exposed, one or more of a primary excitation light source or a secondary excitation light source may be focused to excite one or more blood vessel of the conjunctiva. The secondary light source may be used to determine a reference blood volume, for example by measuring the amount of a reference blood constituent, for example hemoglobin or albumin, at the focal point and calculating a volume based on the steady-state concentration of the reference blood constituent in patients. The primary excitation light source may be used to determine the concentration of a desired biomarker, for example cTnI or glucose, with respect to the reference blood volume. The primary and secondary excitation light sources may for example comprise one or more LEDs or laser diodes. The primary and secondary excitation light sources may comprise one or more wavelength chosen so as to create a desired response of a blood constituent, for example a strong (e.g. nearly optimal) reflectance, fluorescence, absorbance, IR absorbance, or resonance Raman response. In some embodiments, the camera may be configured with an optic to view the blood vessels of a region of the eye in order to align the primary and secondary light beams at a region of the eye such that beams are focused together on a tissue volume of the region.

The backscattered light from the eye may be collected by an optical system comprising backscatter collecting optics before passing to one or more of a primary detector or secondary detector. The backscatter collecting optics may for example comprise a Schwarzschild reflective optics, a dichroic or partial mirror, and an optical wavelength separator as described herein such as one or more narrow band wavelength filters, gratings, prisms or an etalon. The detectors may for example comprise photometric photodiodes or semiconductor photomultipliers. One embodiment of a backscatter collecting optics is shown in greater detail in FIG. 5.

Electrical signals generated by the primary and secondary detectors may be sent for signal conditioning by one or more signal conditioning circuits. Signal conditioning may comprise one or more of amplification, filtration, or offset correction. The analog output of the signal conditioning circuits may be visualized using an oscilloscope at a test point. The analog output of the signal conditioning circuits may be fed into a sample and hold analog to digital converter ("S&H-ADC") of a micro-controller. The micro-controller may act as a controller for the device 300 and may comprise a processor to process one or more detected and conditioned signals. The processor may be configured with instructions to determine the amount of biomarker from the signals generated by the primary and secondary detectors. The micro-controller may control the timing of activation of one or more light sources. Minimum time intervals for device triggering may be set in the micro-controller, for example in the processor, to ensure that the signals collected represent the same location of the eye. The processor may control the timing of the signal or image acquisition. The processor may carry out the signal processing. Signal processing may comprise one or more of calibration, digital filtering, signal averaging, signal extraction, data storage, data transfer, data transmission, or data display. The micro-controller may for example be interfaced to a computer, for example a laptop computer. The micro-controller may monitor one or more user input controller and respond to user instructions. User instructions may for example include turning the device on or off, directing the device to measure the concentration of a biomarker, directing the device to recall a previous measurement from a data storage unit, or directing the device to store data for later recall. The micro-controller may be connected to a data transmission unit to transmit data to an external system and provide for software updates. The data transmission unit may for example be wired or wirelessly connected to the micro-controller. The micro-controller may control one or more displays to provide the user, for example the patient or caregiver, with feedback on the measurements. Feedback may for example include one or more of the reference blood constituent measurement, the reference blood volume, the biomarker measurement, the biomarker concentration, instructions to the user, or error codes. The device 300 may be powered by a power unit. The power unit may comprise a low DC voltage applied through a standard universal power adaptor.

The circuitry can be configured in many ways to determine the amount of the constituent, and can be configured with one or more of local processing with a processor on the support, local processing with a local processor such as a smart phone or a remote server, and the data can be transmitted wirelessly among any of these processors.

The processor mounted on the support such as the head worn support or table support can be configured to control the light sources and measure signals from the detectors. The processor mounted on the support will typically comprise analog to digital conversion circuitry to measure the signals from the detectors. The circuitry on the support can be configured to measure the signals from the detectors to measure the amount of light energy received with the detectors. The processor on the support can be coupled to or may comprise communication circuitry such as wireless communication circuitry to transmit the measurements to a remote server. The measurement data can be transmitted to the remote server with WiFi, or wireless communication, such as pairing, with a user device such as a smartphone, tablet or personal computer, which can transmit the data to the remote sever.

The configuration of one or more processors to determine of the amount of the constituent measured with resonance Raman can be configured in many ways. For example, the processor on the support can be configured to determine the amount of the constituent measured with resonance Raman in response to the reference beam as described herein. The amount determined with the processor on the support can be output to a display, such as a display on a smart phone, tablet or personal computer in wireless communication with the spectrometer as described herein. Alternatively, the processor electronically coupled to the detectors can be configured to transmit the measurement data to another local processor such as a tablet, smart phone or personal computer to determine the amount of the constituent. This measurement data along with a user identification such as a patent identification can then be transmitted to a remote server such as an electronic medical records ("EMR") database. In yet another configuration, the local processor electronically coupled to the detectors can be configured to transmit the data to a remote server for the remote server to determine the amount in response to the resonance Raman and reference signal measurements from the detectors, and the determined amount can be transmitted from the remote server to a display visible to the user.

The distributed processing arrangement can be used to provide updates, provide a user friendly interface, and decrease the overall cost and complexity of the system. A mobile computing device such as a tablet or smart phone with a touch screen user interface may comprise a software application ("app"), downloadable from a vendor, such that the app can be installed on the mobile computing device. The mobile computing device may comprise downloaded software instructions to communicate with the processor on the support and to communicate with the remote server, for example. The mobile computing device and processor on the support may be configured to allow software updates to the processor on the support, such as firmware updates or other software updates of the computer on the support. The downloaded software app may comprise instructions for wireless communication of data between the spectrometer processor and the processor of the mobile computing device. The downloaded software app may comprise instructions to display the amount of the constituent measured with the resonance Raman peaks. Alternatively or in combination, the downloaded software app may comprise instructions to determine the amount of constituent from spectrometer data of the measured resonance Raman peaks and the data from the reference beam transmitted by the processor electronically coupled to the detectors, and to display the amount of the constituent to the user. The downloaded software app may comprise instructions to transmit this data to a remote server for the remoter server to determine the amount and to receive the amount from the remote server and display the amount.

Figure 4:
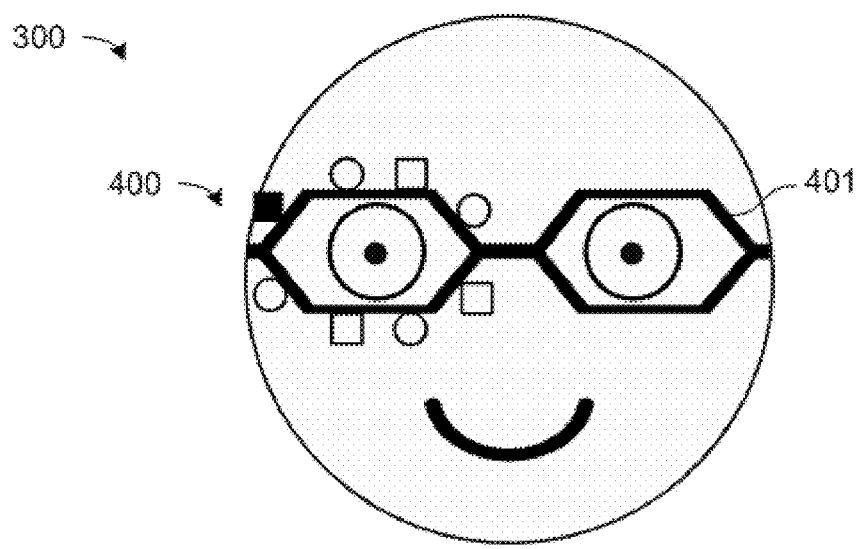
FIG. 4 shows a schematic of an eye positioning system, in accordance with embodiments.

FIG. 4 shows a schematic of an eye positioning system. The device 300 may be configured so as to be worn by a patient. The non-invasive spectral detector device 300 may comprise a support 401 shaped to couple to the patient or subject and support the device 300 with the head of the patient. The support 401 may be configured to support the primary light source, the secondary light source, the optical system, the primary detector, and the secondary detector. The support 401 may be further configured to support the processor, a power supply, and wireless communication circuitry. The support 401 may be configured to support the eye positioning system as described herein. The support 401 may comprise one or more of an eyeglass frame, a helmet, goggles, or a spiral extension to wrap around the head of the patient. The device 300 may comprise the head worn support 401, the primary resonance Raman light source, the secondary reference light source, the optical system, the primary resonance Raman detector, the secondary reference detector, the processor, the power supply, and the wireless communication circuitry and be configured with a weight such that it may be worn comfortably by the patient. The device 300 may have a weight within a range of about 125 grams to about 1 kilogram. The device 300 may have a weight within a range of about 125 grams to about 750 grams. The device 300 may have a weight within a range of about 125 grams to about 500 grams. The device 300 may have a weight within a range of about 125 grams to about 250 grams. Although not necessary, at least some of the processing of the spectral data signals from the detectors can be performed with a processor not mounted on the head of the user in order to further decrease the weight if helpful. The processor and power supply may be located away from the primary and secondary light sources, the primary and secondary detectors, and the optical system in order to distribute the weight of the support when placed on the head of the subject. The processor may be configured to transmit data as described herein. The support 401 may comprise a cover as previously described herein to inhibit ambient light from illuminating the tissue.

The support 401 may comprise an eye positioning system 400 to ensure that the eye attains the proper eye position prior to biomarker excitation and signal detection. The eye positioning system 400 may for example comprise a first positioning light source in order to illuminate the tissue of the eye during positioning. The first positioning light source may comprise one or more near IR (NIR) or IR LEDs. Light in the NIR or IR spectra have different reflectance and absorbance properties at different locations in the eye, with the iris, pupil, and conjunctiva (and sclera) having differing properties. These differences may be used to determine the position of the eye, for example the position of the iris or pupil. Light reflected by the eye may be detected by one or more detectors, for example a small NIR video camera or photodiode. The detectors may be configured to detect the proportions of light reflected by the eye. Signal processing of these proportions may provide a description of the location of the eye. Motion of the eye may result in changes in the reflected light measured by the detectors and thus the processed signal may be compared to previous signals to determine the changes to the position of the eye.

The eye positioning system 400 may be used to identify the position of the eye and move the excitation optics into an optimal excitation position relative to the eye. One or more images of the conjunctiva may be acquired by the eye positioning system and manually or automatically analyzed to identify the blood vessels of the conjunctiva, extract the optimal x-y position, and adjust the position or aim of the one or more excitation light sources to the desired position for optimal excitation results.

Alternatively or in combination, the eye positioning system 400 may be used to direct the eye to move to the proper eye position. The position of the eye may be determined directly by a caregiver for example. The device 300 may for example offer a window or door which may be used by an operator to directly view the position of the eye of the patient. The patient may be asked to move the eye in a specified direction, for example towards the top, bottom, left or right of the device. Once the proper eye position has been reached, the measurement chamber of the device may be sealed off from external light.

Alternatively or in combination, the eye positioning system 400 may comprise a second positioning light source to act as a visual illuminator and project a light beam at a spot beyond the eye, for example below the ridge of the nose, in order to guide the gaze of the patient such that the eye is moved into the proper eye position and aligned with the optical system of device 300. The second positioning light source may for example provide a visible illuminator on a first side of the eye on the support or the side of the nose. The second positioning light source may comprise a visible LED, for example a green LED. The patient may be asked to look at the visible illuminator to direct the gaze into the proper eye position. The patient may be asked to look above, below, left, or right of the visible illuminator to direct the gaze into the proper eye position. The excitation light sources and detectors may be located on a second side of the eye on the support in order to measure blood at the conjunctiva of the eye when the eye is moved into the proper eye position in response to directions to view the visible illuminator.

The proper eye position may be the eye position at which the blood vessels of the conjunctiva are exposed to an excitation light beam of the device perpendicularly. The proper eye position may be the eye position at which the largest blood vessel or largest blood vessels of the conjunctiva are exposed to an excitation light beam of the device perpendicularly. The proper eye position may be the eye position at a sufficient blood vessel density of the conjunctiva are exposed to an excitation light beam of the device perpendicularly. The proper eye position may differ from patient to patient. The proper eye position may not include the iris or the pupil in the excitation beam path. The proper eye position may be determined by repeated measurements of the eye to determine the position of the eye at which a strong spectral signal may be obtained. The proper eye position may for example be determined by directing the eye to look at a visible illuminator generated by a green LED, pulsing the NIR LEDs at the eye, collecting the reflected or backscattered light with the photodiodes, and determining the position of the eye by comparing the relative intensities of the returning light with a processor. The proper eye position may be stored for repeated measurements of the patient over time. Ensuring that the eye is in the proper eye position may promote the safety of the subject by preventing vulnerable parts of the eye, such as the iris or the pupil, from overexposure to irradiation from the excitation light sources. The device 300 may be configured such that the excitation light sources are not activated until the eye is in the proper eye position to provide a built-in safety mechanism.

While device 300 comprising a wearable support 401 is shown in FIG. 4, the device 300 may comprise a support 401 configured to for placement on a tabletop. The tabletop spectrometer 300 may comprise an eye positioning system 400 substantially similar to the embodiments described herein. The support 401 of the tabletop spectrometer 300 may be shaped to support a chin of a patient in order to align the eye with the optical components of device 300 (e.g. the primary and secondary light sources, the optical delivery system, or the primary and secondary detectors).

FIG. 5 shows a schematic diagram of a non-invasive spectral detection device 300 highlighting the optical system and excitation light paths. The spectral detection device 300 may comprise a micro spectral-detector system 500 comprising a primary light source, a secondary light source, an optical system or backscatter collecting optics, a primary detector, and a secondary detector. The device 300 may further comprise an eye positioning system 400 as previously described herein, for example a video camera and first positioning light source. The micro spectral-detector system 500 of the device 300 may be aligned with the eye 100 when the eye 100 is in the proper eye position so as to generate a strong response from the blood vessels of the conjunctiva when the micro spectral-detector system 500 is activated. One or more of the components of the micro spectral-detector system 500 may comprise a removable, replaceable, or interchangeable component as described herein.

The micro spectral-detector system 500 may be used to determine a reference volume of blood for one or more of the exposed blood vessels of the conjunctiva 101. Because the amount of blood may vary depending on the exact focal point of the excitation light sources of the micro spectral-detector system 500, a reference measurement of a stable, readily-available reference blood constituent may be used to determine the blood volume at the focal point and calculate a blood concentration of a biomarker as described herein. The reference blood constituent may be a blood constituent which maintains a known, stable concentration in the blood and is abundant so as to be easily measured, for example hemoglobin or albumin. The reference blood volume may be used to calculate the concentration of a desired biomarker.

Measurement of blood volume may comprise emission of a light beam from a secondary light source and detection of backscattered light from the blood vessels of the conjunctiva 101 by a secondary detector. The secondary light source may be configured to focus the light energy on a blood vessel beneath the epithelium of the conjunctiva. Light energy may be transmitted toward the excitation region in a substantially collimated configuration. The secondary light source may for example comprise an LED or a laser diode. The secondary detector may comprise a photometric photodiode, a semiconductor photomultiplier, a charge-coupled device (CCD), or a complementary metal-oxide semiconductor (CMOS) photo array for example. The reference blood constituent may cause backscattering of the light through the epithelium to the backscatter collecting optics or optical system. The backscatter collecting optics or optical system may comprise a focusing element, for example a Schwarzschild optics as shown herein, which collects the backscattered light from the illuminated region of the eye and directs the backscattered light to the secondary detector. The backscatter collecting optics may comprise one or more of a lens, an objective lens, a reflector, a curved reflector, a spherical reflector, a curved reflector with an aperture, a concave reflector with an aperture, a convex reflector, a convex reflector aligned with an aperture of a concave reflector, or a Schwarzschild optics. The backscatter collecting optics may be used to focus the backscattered light received from the excitation region and transmit it in a substantially collimated configuration toward the secondary detector. A wavelength separator as described herein, for example a filter, may be used to filter out undesired wavelengths, for example those wavelengths not characteristic of the reference blood constituent, prior to the collimated light beam reaching the secondary detector. The secondary detector may be coupled to a processor configured with instructions to determine the blood volume from the reference blood constituent measurement. The intensity of the light detected by the secondary detector may be correlated to an expected concentration of the reference blood constituent in order to determine the blood volume and provide a reference for comparison for the measured biomarker peak intensities. The reference blood constituent measurement may occur prior to or at the same time as measurement of a desired biomarker by a primary light source and a primary detector.

The amount of blood measured may be used to confirm that the eye is in the proper eye position, for example to confirm the presence of one or more blood vessels at the focal point of the light beam of the device. Confirmation of the presence of blood vessels may be used to ensure the safety of the wearer and prevent further device activity if there are no blood vessels present, for example if the eye has moved from the proper eye position. When the reference blood measurement occurs prior to excitation of the biomarker, the processor may be configured to prevent activation of the primary light source when the illuminated tissue contains no or few blood vessels or when the eye is determined to have moved from the proper eye position. The eye may be repositioned and the presence of blood vessels may be confirmed with the secondary light source and secondary detector before excitation of the tissue with the primary light source and detection of the biomarker signal by the primary detector. When the reference blood measurement occurs during excitation of the biomarker, the processor may be configured to halt activity of the primary light source when the illuminated tissue contains no or few blood vessels or when the eye is determined to have moved from the proper eye position. The eye may be repositioned using the eye positioning system as previously described before resuming excitation of the tissue.

The micro spectral-detector system 500 may be used to determine a concentration of a biomarker in the blood of the conjunctiva. Measurement of the concentration of a specific biomarker may comprise emission of a light beam from a primary light source and detection of backscattered light from the blood vessels of the conjunctiva 101 by a primary detector. Light energy may be transmitted toward the excitation region in a substantially collimated configuration. The primary light beam and the secondary light beam be may be arranged in a coaxial configuration so as to be directed along a common axis toward the excitation region. The primary light beam and the secondary light beam be may be arranged in a confocal configuration so as to focus the light beams together on a tissue volume of the excitation region. The primary light source may for example comprise an LED or a laser diode. The primary detector may comprise a photometric photodiode, a semiconductor photomultiplier, a charge-coupled device (CCD), or a complementary metal-oxide semiconductor (CMOS) photo array for example. The primary light source may be configured to focus the light energy on a blood vessel beneath the epithelium of a region of the conjunctiva. The biomarker may cause backscattering of the light through the epithelium to the backscatter collecting optics. The backscatter collecting optics may comprise a focusing element, for example a Schwarzschild optics as shown herein, which collects the backscattered light from the illuminated region of the eye and directs the backscattered light to the primary detector. The backscatter collecting optics may be used to focus the backscattered light and transmit it in a substantially collimated configuration toward the primary detector. The backscattered light from the primary light source may be transmitted coaxially with the backscattered light from the secondary light source along an optical path. A wavelength separator, for example a dichroic mirror, may be positioned in the light path between the backscatter collecting optical system and the detectors in order to separate the reference backscattered light from biomarker backscattered light. The reference signal comprising the reference backscattered light may be directed toward the secondary detector while the biomarker signal comprising the biomarker backscatter light may be directed toward the primary detector. A wavelength separator as described herein, for example a filter, may be used to further filter out undesired wavelengths, for example those wavelengths not characteristic of the biomarker, prior to the light reaching the primary detector. The primary detector may be coupled to the processor configured with instructions to determine the amount of the biomarker in response to the light received by the primary detector. The intensity of the light detected by the primary detector may be correlated, for example by the processor, to the intensity of the reference blood constituent measurement, for example the reference blood volume, in order to determine the concentration of the biomarker. The concentration of the biomarker may comprise the amount of biomarker per unit volume of blood.

One or more of the primary or secondary light sources may be located below the light collimator of the backscattered light collector as shown herein. One or more of the primary or secondary light sources may be located outside of the backscattered light optical system and the light beam(s) may be delivered via optical fibers with collimating lenses for example.

The primary light source may be configured to focus a short pulse of light to the conjunctiva. The light beam may be a spectrally narrow band, for example a monochromatic light beam comprising a bandwidth of no more than about ten nanometers. The light beam may be a spectrally narrow band, for example a monochromatic light beam comprising a bandwidth of no more than about three nanometers. The primary light beam may be a measurement beam. The primary light source may for example be a tunable laser comprising a bandwidth of no more than about a nanometer when tuned to a wavelength. The primary light source may emit a narrow bandwidth light beam with a peak value selected to be at or near the electronic transition or excitation of the biomarker so as to generate resonance. The electronic excitation of the biomarker may correspond to a precisely excited state of the biomarker. The primary light beam may be a monochromatic light beam comprising one or more wavelengths having a frequency at or about an electronic excitation of the biomarker so as to generate resonance, for example resonance Raman peaks. The electronic excitation of the biomarker corresponding to resonance Raman scattering may be above a virtual state corresponding to Raman emission of the biomarker. The maximum irradiance of the secondary excitation beam may be within the limits of the applicable laser and non-coherent light source standards. The maximum irradiance of the primary excitation beam may be within the limits of the applicable laser and/or non-coherent light source standards. The energy of the primary excitation beam may exceed an eye safe threshold. The primary light source may be a higher intensity or higher powered light source than the secondary light source, for example when the expected concentration of the biomarker of interest is lower than the expected or known concentration of the reference blood constituent. The primary light beam may be a higher intensity or higher powered light beam than the secondary light beam.

One or more of the primary detector or secondary detector may for example be configured to measure absorption of an excitation region of the conjunctiva. One or more of the primary light source or secondary light source may for example be an NIR or IR LED or laser diode with a peak value selected to be at or near the absorption peak of the biomarker and one or more of the primary detector or the secondary detector may be configured to detect the amount of NIR or IR absorption from the backscattered light. One or more of the primary light source or secondary light source may for example be an NIR or IR LED or laser diode with a peak value selected to be at or near the absorption peak of the biomarker and one or more of the primary detector or the secondary detector may be configured to detect the spectra of NIR or IR absorption from the backscattered light.

The primary light source may for example be an LED or laser diode with a peak value selected to be at or near the electronic transition of the biomarker so as to generate one or more resonance Raman peaks and the primary detector may be configured to selectively detect one or more resonance Raman peaks from the backscattered light. The primary light source may for example be a broadband light source and the primary detector may be configured for Fourier transform infrared spectroscopy measurements.

In many embodiments, the device 300 may be configured to detect the concentration of a specific biomarker, for example cTnI, using resonance Raman spectroscopy. Light incident on the conjunctiva may excite Rayleigh scattering, fluorescence, and Raman scattering of the blood. The primary light source may be may comprise one or more wavelengths having a frequency at or near the frequency of an electronic transition (e.g. resonance Raman frequency) of the biomarker. Use of a primary light source at the resonance Raman frequency may greatly amplify the resonance Raman response of the biomarker (up to $10^6$ times higher than standard Raman spectroscopy) and allow for detection of biomarkers which exist in the blood at concentrations too low to be detected by standard Raman spectroscopy techniques. A secondary light source may be chosen so as to excite a reference blood constituent, for example hemoglobin, before or at the same time as the primary light source excites the biomarker. The primary and secondary light sources may shine one or more short pulses of light focused at the same location of the conjunctiva of the eye. The light beams may be focused so as to illuminate one or more blood vessels of the conjunctiva. Backscattered light from the conjunctiva may be collected the backscattered light collector, focused on the returned light collimator, and passed through an exit hole in the backscattered light collector in a substantially collimated configuration. The backscattered light may comprise one or more of the light scattered by the biomarker or the light scattered by the reference blood constituent. The backscattered light collector may for example comprise a dichroic mirror in order to reduce the back-reflected excitation light sent to the detectors. A wavelength separator, for example a dichroic mirror, may be positioned in the light path between the backscatter collecting optical system and the primary and secondary detectors in order to separate the non-resonance Raman signals generated by the reference blood constituent from the resonance Raman signals generated by the biomarker. The resonance Raman peaks may be transmitted by the wavelength separator to the primary detector. The wavelength separator may comprise one or more of a prism, a grating, a mirror, an etalon, an optical filter, or a plurality of optical filters. The wavelength separator may be configured to direct (for example reflect) nearly 100 percent of the resonance Raman signal from the biomarker to the primary detector. The wavelength separator may be configured to direct the remaining backscattered light, including the reference blood constituent signal, towards the secondary detector. The primary detector may be narrow band filtered to selectively detect one or more resonance Raman peak of the biomarker. The primary detector may comprise a plurality of detectors, each configured to detect one or more resonance Raman peak of the characteristic signature of the biomarker. The secondary detector may be narrow band filtered to selectively detect the spectral response of the reference biomarker in the non-resonance Raman portion of the light. The secondary detector may comprise a plurality of detectors, each configured to detect a portion of the spectral response of the reference biomarker. The blood concentration of the biomarker may be calculated from the intensity of the resonance Raman signal relative to the intensity of the reference blood constituent signal or the blood volume calculated therefrom. The biomarker and reference blood constituent may be measured repeatedly so as to improve the signal-to-noise ratio and measurement accuracy. The biomarker and reference blood constituent may be measured repeatedly so as to monitor the concentration of the biomarker over time to determine changes in concentration (for example increases or decreases) over time.

Figure 6:
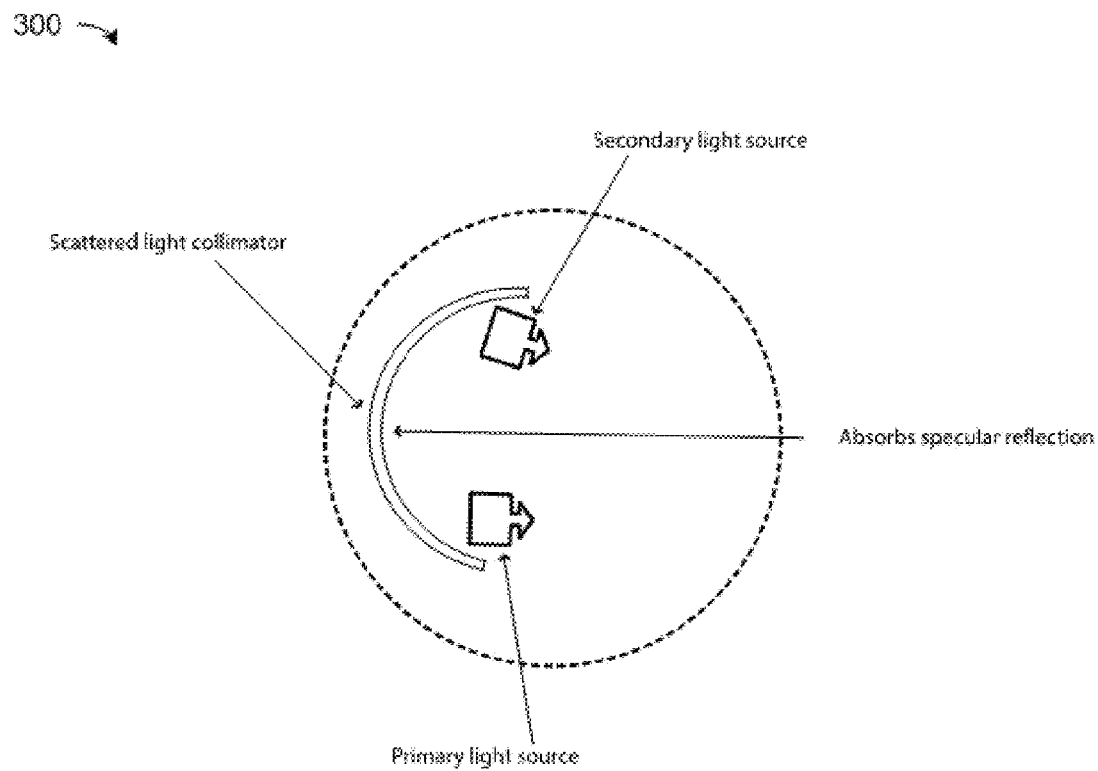
FIG. 6 shows a scattered-light collimator, in accordance with embodiments.

FIG. 6 shows the scattered light collimator of device 300 in greater detail. The primary and secondary light sources may be small enough so as to be situated between the scattered light collimator and the eye. The primary and secondary light sources may each project a beam of light focused onto the same location of the conjunctiva. The primary and secondary excitation light beams may be concentric and have the same diameter so as to expose the same volume of blood to illumination with each measurement iteration. The blood vessels of the conjunctiva may be illuminated by the primary and secondary light beams and light may be scattered back towards the scattered light collimator in response the presence of the biomarker and reference blood constituent, respectively. The scattered light may comprise Rayleigh scattering, fluorescence, and Raman scattering. Light may also be specularly reflected off of the eye. Specular reflection may dilute the signals from the biomarker and reference blood constituent, therefore the scattered light collimator may be configured to absorb specular reflection from the primary and secondary light sources and prevent contamination of the backscattered light with specularly reflected light.

The spectrometer 300 may be configured to detect a specific blood constituent or biomarker in the blood in a non-invasive in vivo manner. Blood biomarkers may for example be Glucose, Troponin Complex, Troponin T (TnT), Troponin I (TnI), Troponin C (TnC), a cardiac biomarker, a Troponin cardiac biomarker, a breast cancer biomarker, Breast Cancer 1 Biomarker (BRCA1), Breast Cancer 2 Biomarker (BRCA2), a biomarker related to coronary disease, B-type Natriuretic Peptide (BNP) and N-terminal proBNP (NT-proBNP), an infection specific biomarker, a biomarker related to dementia, Beta Amyloid, Low Density Lipoprotein (LDL), High Density Lipoprotein (HDL), Cholesterol, a Triglyceride, a Thyroid Stimulating Hormone (TSH), Creatine Kinase, Prostate Specific Antigen (PSA), Creatinine, Globulin, Adenovirus DNA, Alanine Aminotransferase (ALT/SGPT), Albumin, Alkaline Phosphatase (ALP), Alpha-1-Acid Glycoprotein, Alpha-1-Antitrypsin, Alpha-Fetoprotein (AFP), Amphetamines, Amylase, Androstenedione, RBC Antibody Detection, Anti-Mullerian Hormone (AMH), Antinuclear Antibodies, Apolipoprotein (apo A-1, apo B), Apolipoprotein A-1 (apo A-1), Apolipoprotein B (apo B), Aspartate Aminotransferase (AST/SGOT), B Cell, Barbiturates, Benzodiazepines, Beta-2 Microglobulin, Bilirubin, Blood Type (ABO/RhD), Blood Urea Nitrogen (BUN), Borrelia Antibody (Lyme Disease), Calcitonin, Calcium, Cancer Antigen 125 (CA 125), Cancer Antigen 15-3 (CA 15-3), Cancer Antigen 27.29 (CA 27.29), Cancer Antigen-GI (CA 19-9), Carbon Dioxide, Carcinoembryonic Antigen (CEA), Cardiolipin Antibody (ACA), CBC (Complete Blood Count), CD4, CD8, Celiac Panel, Chlamydia Trachomatis, Gonorrhea, Chloride, Cholinesterase, Cocaine, Complement Component 3 antigen, Complement Component 4 antigen, Cortisol, C-Peptide, C-Reactive Protein (CRP), Cyclic Citrullinated Peptide (CCP) Antibody, Cyclosporine A, Cystatin C, Cytomegalovirus (CMV) Antibody, Cytomegalovirus (CMV) Antibody, D-Dimer, Deamidated Gliadin Peptide (DGP) Antibody, Deamidated Gliadin Peptide (DGP) Antibody, Dehydroepiandrosterone Sulfate (DHEA-S), Deoxypyridinoline crosslinks (DPD) (Collagen crosslinks), Double-stranded DNA (dsDNA) Antibody, EBV Early D Antigen (EA-D), EBV Nuclear Antibody, EBV Viral Capsid Antigen (VCA), EBV Viral Capsid Antigen (VCA), Ecstasy (MDMA), Endomysial Antibody (EMA), Endomysial Antibody (EMA), Epstein-Barr (EBV) Antibody, Erythrocyte Sedimentation Rate (ESR/Sed Rate), Estradiol, Estriol, Estrone, Ethanol, Extractable, Ferritin, Fibrinogen, Folate (Folic acid), Follicle Stimulating Hormone (FSH), Gamma-Glutamyltransferase (GGT), Gastrin, Glucose, Growth Hormone (HGH), chronic Haptoglobin (hCG), *Helicobacter Pylori* (*H. Pylori*), Hematocrit (HCT), Hemoglobin (HGB), Hemoglobin A1c (HbA1c), Hemogram 2, Hepatitis A (HAV) Antibody, Hepatitis A (HAV) Antibody, Hepatitis B (HBV) Core Antibody, Hepatitis B (HBV) Core Antibody, Hepatitis B (HBV) Surface Antibody (HBsAb), Hepatitis B (HBV), Hepatitis C (HCV) Antibody, HER-2/neu, Herpes Simplex 1 (HSV1), Herpes Simplex 2 (HSV2), HIV-1, Homocysteine, IGF-1 (Insulin-like Growth Factor 1), Insulin, Iron, Lactate Dehydrogenase, Lead, Lipase, Lithium, Luteinizing Hormone (LH), Magnesium, Marijuana (THC), Measles, Mumps, and Rubella (MMR) Immunity, Methadone (dolophine), Methamphetamines, Microalbumin, Mumps Antibody, Myoglobin, N. Gonorrhea, Natural Killer Cells, Nuclear Antigen Antibody Jo-1, Nuclear Antigen Antibody RNP, Nuclear Antigen Antibody Scl-70, Nuclear Antigen Antibody Sm, Nuclear Antigen Antibody SSA, Nuclear Antigen Antibody SSB, Opiates, Parathyroid Hormone (PTH), Phencyclidine (PCP), Phosphorus, Platelets, Potassium, Prealbumin, Progesterone, Prolactin, Propoxyphene, Reticulocyte Count, Rheumatoid Factor, Rubella Antibody, Rubeola (Measles) Antibody, Sex Hormone-binding Globulin (SHBG), Sodium, Streptolysin O Antibody, Treponema Pallidum Antibody, T Cell, Triiodothyronine (T3), Testosterone, Thyroglobulin, Thyroglobulin Antibodies (TAA), Thyroid Peroxidase (TPO) Antibody, Thyroxine Binding Globulin (TBG), Thyroxine (T4), Tissue Transglutaminase (tTG) Antibody, Toxoplasma, Transferrin, Treponema Pallidum Antibody, Triiodothyronine (FT3), Uric Acid, Varicella-Zoster (VZV) Antibody, Vitamin B-12, Vitamin D 25-OH, or WBC.

Based on the teachings described herein, a person of ordinary sill in the art may configure the device 300 for other blood constituents, including newly-identified blood constituents, for example newly-identified cancer-related biomarkers.

The resonance excitation wavelength of a specific biomarker may be determined by illuminating the specific biomarker in vitro with a tunable laser and using a spectroscope to collect the Raman spectra backscatter from the sample as the laser is tuned over multiple wavelengths. The laser may be tuned so as to excite the biomarker along the entire visible spectrum or along a portion of the visible light spectrum. The collected spectra may be processed as described previously herein in order to identify one or more absorption or resonance peaks which make up the characteristic peak signature of the biomarker. In resonance Raman spectroscopy the excitation of a particular spectral response of a particular blood constituent may be highly enhanced by resonance in both response amplitude and specificity. At resonance, multiple peaks may be emitted which are characteristic of a particular biomarker. The spectrum of the peak signature of the biomarker may be compared to other known spectra of blood constituents to identify the resonance Raman peaks best suited for in vivo separation and detection. The excitation wavelength at which the characteristic peak signature reaches a maximum intensity may be considered the resonance Raman frequency of the biomarker (e.g. the excitation frequency at or near the frequency of an electronic transition or excitation of the biomarker). The excitation wavelength at which the characteristic peak signature is best distinguished from other blood constituents may be considered the resonance Raman frequency of the biomarker. Blood is a very complex chemical mixture with many organic constituents which may have similar spectral responses, for example similar or partially overlapping Raman spectra, similar or partially overlapping fluorescence, similar or partially overlapping NIR absorbance, or any combination thereof.

After identifying the resonance Raman frequency and one or more peaks characteristic of the biomarker, the device 300 may be configured with a primary light source to generate a light beam with a peak wavelength at or near the resonance Raman frequency of the biomarker to generate resonance Raman peaks. The backscattered light may be passed through one or more optical wavelength separators in order to selectively transmit the identified one or more resonance Raman peaks to the primary detector. The primary detector may be configured to detect wavelengths at or near the one or more Raman peak for identification of the biomarker. The process of identifying and selecting the resonance Raman frequency and resonance Raman peak(s) may be repeated for each biomarker of interest, including those newly-identified in the scientific literature. Each biomarker may have a dedicated primary light source and primary detector specifically selected for the resonance Raman properties identified of that biomarker.

More than one spectral peak of the biomarker of interest may be measured by one or more primary detector configured to selectively detect one or more peak from the backscattered resonance Raman signal. The backscattered light may for example be split so as to project partial beams on the one or more primary detectors. For example, the light may be split so as to direct a first portion of the resonance Raman signal to a first primary detector for detection of a first Raman peak and a second portion of the resonance Raman signal to a second primary detector for detection of a second Raman peak. Alternatively or in combination, optical narrow band filters may be applied at the surface of a multi-pixel primary detector, for example a charge-coupled device (CCD), a complementary metal-oxide semiconductor (CMOS), or semiconductor photomultiplier. Alternatively or in combination, several filters and several primary detectors may be used to detect the characteristic resonance Raman peaks of the biomarker.

Figure 7:
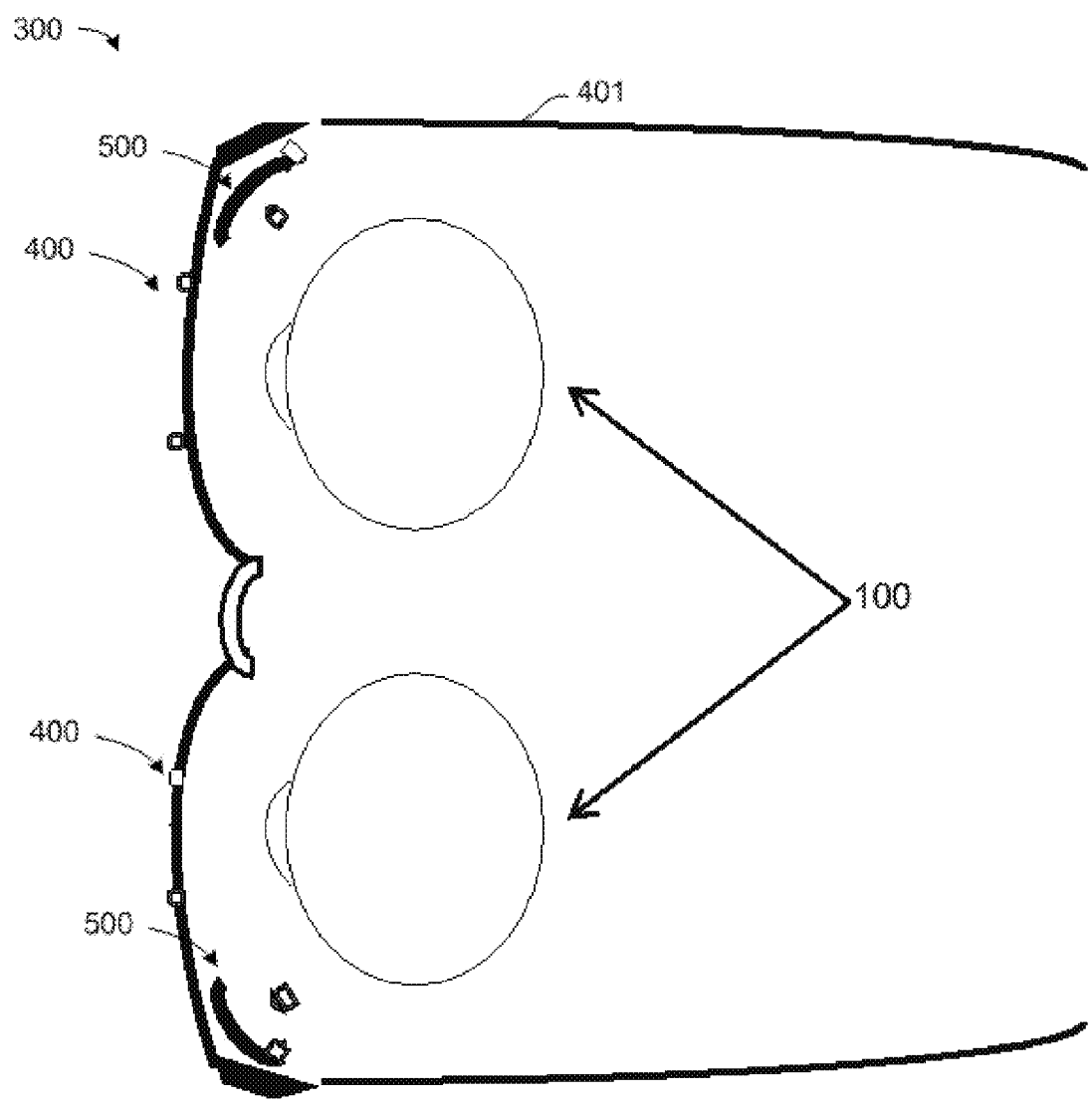
FIG. 7 shows a top-view of a non-invasive spectacle-mounted spectral detector, in accordance with embodiments.

FIG. 7 shows a top-view of a non-invasive spectacle-mounted spectral detector. The device 300 may comprise a support 401 as previously described herein, for example a pair of spectacles. The device 300 may be configured to detect one or more biomarkers in the blood vessels of the conjunctiva of a patient. The exemplary embodiment shown here comprises two eye positioning systems 400 and two micro spectral-detector systems 500. The eye positioning systems 400 may be mounted on the front part of the spectacle frame 401. The eye positioning systems 400 may be configured to position one or both of the eyes into a proper eye position as previously described herein. The elements of the eye positioning systems 400, for example LEDs and photodiodes, may be positioned around the circumference of the frame 401 as illustrated in FIG. 4. The micro spectral-detector systems 500 may be mounted adjacent to the hinges of the spectacle frame 401. The eye positioning systems 400 and micro spectral-detector systems 500 may be controlled by the timing and signal processing electronics as described previously herein. One or both of the eye positioning systems 400 may be activated when the user turns on the device 300. Detection of the proper eye position may send a signal to the timing and signal processing micro-controller to trigger the primary and secondary light sources of one or both of the micro spectral-detector systems 500 for biomarker and reference blood constituent detection.

The micro spectral-detector systems 500 may be configured to detect the same biomarker, for example to monitor the concentration of the biomarker by repeating measurements in an alternating regime in both eyes. The micro spectral-detector systems 500 may be configured to detect different biomarkers, for example to monitor two related biomarkers for diagnostic purposes. The micro spectral-detector systems 500 may be configured to detect different biomarkers, for example to monitor two unrelated biomarkers for diagnostic purposes.

FIG. 8 shows a side view and a top view of a non-invasive spectral detection system for detection of multiple biomarkers. The device 300 may be configured so as to measure one or more biomarker in reference to one or more reference blood constituent. Each biomarker may have a dedicated primary excitation light source and a dedicated primary detector. For example, a detection system capable of detecting three biomarkers may have three primary excitation light sources and three primary detectors. The optical system may similarly be tailored to each biomarker by providing different dichroic mirrors and/or narrow band pass filters along the light path of each primary and secondary light source specific for each biomarker. The device 300 may be configured as a carrousel-like structure with arm of the carrousel-like structure being coupled to the other arms of the carrousel-like structure at midpoint about which the arms may rotate or pivot about an axis of rotation so as to bring the optics into alignment with the eye and other components of the spectrometer. Each of the plurality of arms of the carrousel-like structure may be configured to support a micro spectral-detector system 500. Each arm may support one or more of a primary excitation light source, a secondary excitation light source, a collimating lens, a dichroic mirror, a primary narrow band filter, a secondary narrow band filter, a primary detector, or a secondary detector. The primary and secondary excitation light sources may be positioned proximate a primary and secondary optical fiber, respectively, in order to transmit the light to the center of the optical system to be focused at the desired location on the conjunctiva. Alternatively or in combination, the primary and secondary excitation light sources may be positioned inside the backscattered light collimator as previously described herein. Each arm of the carrousel-like structure may be specific to a particular biomarker and a particular reference blood constituent. Rotation of the arms about the axis of rotation may bring the desired primary and secondary light sources and wavelength separators into alignment with the backscatter light collecting optical system. Rotation of the arms may be done manually or may be automatically or electronically controlled by the device controller.

One or more of the components of the micro spectral-detector system 500 may be configured for replacement by a user in order to allow additional constituents to be measured, and the capability can allow the weight of the device to be decreased while allowing many biomarkers to be measured. For example, one or more arms of the support comprising one or more of the light source, the wavelength separator, or the detectors, can be configured for removal and replacement. The user can be provided with a plurality of user replaceable structures, in which each of the removable structures is configured to measure a different constituent with resonance Raman peaks. For example, an arm of the carrousel-like structure may be removable, replaceable, or interchangeable, for example in the form or a cartridge or kit, in order to allow the device 300 to measure multiple biomarkers. Replacement of a first cartridge with a second cartridge may allow a user or caregiver to quickly assess multiple biomarkers in a patient without requiring a different spectrometer for each biomarker of interest. In this way the spectrometer device may be configured to detect and measure the concentration of any number or combination of biomarkers of interest with the same device and the interchangeable components. One or more of the filters or light sources of the micro spectral-detector system 500 may for example be removable. One or more of the components of the micro spectral-detector system 500 on an arm of the carrousel-like structure may for example comprise a removable, replaceable, or exchangeable cartridge. One or more of the arms of the carrousel-like structure may be removable, replaceable, or interchangeable in order to allow the device 300 to measure multiple biomarkers. One or more of the arms of the carrousel-like structure may for example comprise a removable, replaceable, or exchangeable cartridge. The carrousel-like structure may for example comprise a removable, replaceable, or exchangeable cartridge. Each carrousel-like cartridge may for example comprise one or more spectral-detector systems configured to detect one or more biomarkers within a similar spectral range. For example, a first carrousel-like cartridge may be configured to detect one or more biomarkers with similar excitation or emission characteristics and a second carrousel-like cartridge may be configured to detect one or more different biomarkers with similar excitation or emission characteristics different from those of the biomarkers of the first carrousel-like structure.

A person of ordinary skill in the art can configure the specialized spectrometer as disclosed herein to measure the tympanic membrane of a subject.

Digital Processing Devices

As discussed above and herein, the systems, methods, and devices described herein can include one or more digital processing devices, or use of the same. The one or more digital processing devices can be configured to communicate with each other such as with wireless communication. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the systems, methods, and devices disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the systems, methods, and devices disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. The disclosed embodiments and configurations with respect to the measurement of blood shall be considered non-limiting examples, and the spectrometer and apparatus and methods disclosed herein can be configured and used to measure any of the materials disclosed herein. It is intended that the following claims define the scope of the invention and that methods and structures within the scope of these claims and their equivalents be covered thereby.

What is claimed is:

1. A method of non-invasively measuring a blood constituent through an epithelium and vessel walls of blood vessels at a region of a subject with light with a spectrometer, the method comprising:
    generating a monochromatic light beam with a light source, the monochromatic beam comprising a wavelength having a frequency at an electronic excitation of the blood constituent to generate resonance Raman peaks;
    delivering the monochromatic light beam through the epithelium vessel walls to the blood constituent at the region with an optical delivery system;
    receiving with an optical separator light energy from the blood constituent through the epithelium and the vessel walls to selectively transmit the resonance Raman peaks;
    measuring the resonance Raman peaks from the blood constituent at the region with an optical detector;
    generating a reference beam to illuminate blood at the region with the reference light beam;
    measuring a portion of the reference beam backscattered from the blood at the region with a reference detector; and
    determining an amount of the blood constituent from the resonance Raman peaks and the portion of the reference beam backscattered from the blood at the region.

2. The method of claim 1, further comprising determining the amount of the blood constituent from the resonance Raman peaks and the portion of the reference beam backscattered from the blood at the region with one or more of a processor electrically coupled to the detector and the reference detector, a processor of a mobile computing device, or a processor of a remote server.

3. The method of claim 2, wherein the processor is coupled to the light source and the light source transmits the monochromatic light beam to the region with an amount of energy greater than the reference beam, wherein the amount of energy of the monochromatic beam exceeds a retina safe threshold of the measurement beam and the reference beam does not exceed a retina safe threshold of the reference beam, wherein the processor detects a presence of the blood vessels with the portion of the reference beam and transmits the monochromatic beam in response to the presence of the blood vessel, and wherein the processor transmits the reference beam and but not the monochromatic light beam when the presence of the blood vessels has not been detected.

4. The method of claim 2, wherein the processor is coupled to the reference detector and configured to determine one or more of the amount of the constituent or a concentration of the constituent in response to an intensity of the portion of the beam received from the tissue and an intensity of the resonance Raman peaks, the concentration comprising the amount of the constituent per unit volume of the blood.

5. The method of claim 2, wherein the light source, the reference light source, the optical delivery system, the detector and the reference detector are configured to be worn by the subject and are retained with a support shaped to couple to a head of the subject, wherein the support is configured to support the processor and a power supply and communication circuitry and wherein the processor and the power supply are located away from the light source, the reference light source, the optical delivery system, the detector and the reference detector in order to distribute weight of the support when placed on the head of the subject.

6. The method of claim 1, further comprising verifying that a gaze of the subject is directed away from a spectrometer in order to measure a conjunctiva of an eye of the subject by one or more of a measurement beam or an operator of the spectrometer.

7. The method of claim 1, wherein the region comprises a volume of blood and wherein the reference beam measures a second constituent of blood, the second constituent comprising a greater amount by volume than the constituent of interest.

8. The method of claim 1, wherein delivering the monochromatic light beam with the optical system comprises focusing the monochromatic light beam on a blood vessel beneath the epithelium.

9. The method of claim 1, wherein the monochromatic light source is transmitted toward the region in a substantially collimated configuration and wherein the optical system comprises an optical path along which the resonance Raman peaks and the portion are transmitted coaxially toward the detector and the reference detector.

10. The method of claim 1, wherein the monochromatic light beam provides energy at a precisely excited state of the constituent.

11. The method of claim 1, wherein the monochromatic light beam provides energy above a virtual state corresponding to Raman emission of the constituent.

12. The method of claim 1, wherein the light source, the reference light source, the optical delivery system, the detector and the reference detector are configured to be worn by the subject and are retained with a support shaped to couple to a head of the subject.

13. The method of claim 12, wherein the support and the light source, the reference light source, the optical delivery system, the detector and the reference detector weigh no more than about 250 grams.

14. The method of claim 13, wherein the support comprises one or more of an eyeglass frame, a helmet, goggles, a spiral extension to wrap around a head of the subject.

15. The method of claim 12, wherein the support comprises a visual illuminator visible to the user to direct a gaze of the viewer in order to align the tissue with the optical system and wherein the visible illuminator is located on a first side of the eye on the support and the optical system and detector are located one a second side of the eye on the support in order to measure a conjunctiva of the eye when the subject views the visible illuminator.

16. The method of claim 1, wherein the blood vessels are part of a conjunctiva of an eye of the subject or a tympanic membrane of an ear of the subject wherein the epithelium comprises an epithelium of the one or more of the conjunctiva of the eye of the subject or the tympanic membrane of the ear of the subject.

17. The method of claim 1, further comprising measuring one or more of absorption, near infrared light energy, or near infrared spectra of the region with one or more of the reference beam or an additional light beam and one or more of the reference detector or another detector.

18. The method of claim 1, wherein the reference beam comprises a calibration beam, and determining the amount of the constituent in response to a ratio of a resonance Raman signal from the detector to a calibration signal from the portion of the beam received with the reference detector.

19. The method of claim 1, comprising delivering the monochromatic light beam and the reference beam in one or more of a coaxial configuration to direct the monochromatic light beam and the reference beam along a common axis toward the region or a confocal configuration to focus the monochromatic light beam and the reference beam together on a tissue volume of the region.

20. The method of claim 1, wherein a plurality of blood constituents each having different Raman peaks and different resonance Raman excitation wavelengths are measured.

* * * * *